US007030087B2

(12) United States Patent
Gray et al.

(10) Patent No.: US 7,030,087 B2
(45) Date of Patent: Apr. 18, 2006

(54) SYNTHETIC APPROACH TO DESIGNED CHEMICAL STRUCTURES

(75) Inventors: Beulah H. Gray, Ontario, OR (US); Judith R. Haseman, Eagan, MN (US); Kevin Mayo, Minnetonka, MN (US); Arjan W. Griffioen, Maastricht (NL)

(73) Assignee: Regents of the University of Minnesota, Minneapolis, MN (US)

( * ) Notice: Subject to any disclaimer, the term of this patent is extended or adjusted under 35 U.S.C. 154(b) by 424 days.

(21) Appl. No.: 10/300,083

(22) Filed: Nov. 20, 2002

(65) Prior Publication Data

US 2003/0153502 A1 Aug. 14, 2003

Related U.S. Application Data

(60) Division of application No. 09/194,296, filed as application No. PCT/US97/08944 on May 23, 1997, now Pat. No. 6,486,125, which is a continuation-in-part of application No. 08/671,487, filed on Jun. 27, 1996, now Pat. No. 5,955,577, and a continuation-in-part of application No. 08/653,632, filed on May 24, 1996, now Pat. No. 5,830,860.

(51) Int. Cl.
*A61K 38/16* (2006.01)
*C07K 14/00* (2006.01)

(52) U.S. Cl. .......................... 514/12; 530/324
(58) Field of Classification Search ............... 514/12; 530/324
See application file for complete search history.

(56) References Cited

U.S. PATENT DOCUMENTS

| | | | |
|---|---|---|---|
| 5,089,274 A | 2/1992 | Marra et al. |
| 5,171,739 A | 12/1992 | Scott |
| 5,190,873 A | 3/1993 | Lernhardt et al. |
| 5,198,541 A | 3/1993 | Elsbach et al. |
| 5,334,584 A | 8/1994 | Scott et al. |
| 5,348,942 A | 9/1994 | Little, II et al. |
| 5,639,725 A | 6/1997 | O'Reilly et al. |
| 5,786,324 A | 7/1998 | Gray et al. |
| 5,830,860 A | 11/1998 | Gray et al. |
| 5,837,678 A | 11/1998 | Little, II |
| 5,837,682 A | 11/1998 | Folkman et al. |
| 5,854,205 A | 12/1998 | O'Reilly et al. |
| 5,854,214 A | 12/1998 | Little, II |
| 5,856,302 A | 1/1999 | Ammons et al. |
| 5,955,577 A | 9/1999 | Mayo |
| 2002/0146406 A1 | 10/2002 | Mayo |

FOREIGN PATENT DOCUMENTS

| | | |
|---|---|---|
| WO | WO 89/01486 | 2/1989 |
| WO | WO 90/09183 | 8/1990 |
| WO | WO 92/09621 | 6/1992 |
| WO | WO 92/09695 | 6/1992 |
| WO | WO 93/05797 | 4/1993 |
| WO | WO 93/23434 | 11/1993 |
| WO | WO 94/17819 | 8/1994 |
| WO | WO 94/18323 | 8/1994 |
| WO | WO 94/20532 | 9/1994 |
| WO | WO 94/25476 | 11/1994 |
| WO | WO 95/00641 | 1/1995 |
| WO | WO 95/01428 | 1/1995 |
| WO | WO 95/02414 | 1/1995 |
| WO | WO 96/31528 | 10/1996 |
| WO | WO 96/37212 | 11/1996 |

OTHER PUBLICATIONS

Altieri et al., "Association of Biomolecular Systems via Pulsed Field Gradient NMR Self-Diffusion Measurements," *J. Am. Chem. Soc.*, 117, 7566-7567 (1995).
Anisowicz et al., "Constitutive overexpression of a growth-regulated gene in transformed Chinese hamster and human cells." *Proc. Natl. Acad. Sci. USA*, 84, 7188-7192 (1987).
Bangalore et al., "Identification of the Primary Antimicrobial Domains in Human Neutrophil Cathespin G." *J. Biol. Chem.*, 265(23), 13584-13588.
Battafarano et al., "Peptide derivatives of three distinct lipopolysaccharide binding proteins inhibit lipopolysaccharide-induced tumor necrosis factor-alpha secretion in vitro," *Surgery*, 118, 318-324 (1995).
Bax et al., "MLEV-17-Based Two-Dimensional Homonuclear Magnetization Transfer Spectroscopy," *J. Magnetic Resonance*, 65, 355-360 (1985).
Blanco et al., "A short linear peptide that folds into a native stable β-hairpin in aqueous solution." *Structural Biology*, 1, 584-590 (1994).
Bone et al., "A second large controlled clinical study of E5. a monoclonal antibody to endotoxin: Results of a prospective, multicenter, randomized, controlled trial," *Critical Care Medicine*, 23, 994-1005 (1995).
Bottone et al., "Association of *Pseudomonas cepacia* with Chronic Granulomatous Disease," *J. Clin. Microbiol.*, 1(5), 425-428 (1975).
Brown et al., "[8] Chemical Synthesis and Cloning of a Tyrosine tRNA Gene." *Methods in Enzymology*, 68, 109-151 (1979).
Bryson et al., "Protein Design: A Hierarchic Approach," *Science*, 270, 935-941 (1995).
Campanelli et al., "Azurocidin and a Homologous Serine Protease from Neutrophils—Differential Antimicrobial and Proteolytic Properties," *J. Clin. Invest.*, 85, 904-915 (1990).

(Continued)

Primary Examiner—Charles L. Patterson, Jr.
(74) *Attorney, Agent, or Firm*—Mueting Raasch & Gebhardt, P.A.

(57) ABSTRACT

This invention relates to the chemical design and production of peptides, peptide structure and three dimensional conformation was assessed using NMR, circular dichroisin and pulsed field gradient NMR. In addition, this invention relates to peptides produced by these methods and to methods for using the peptides.

21 Claims, 7 Drawing Sheets

OTHER PUBLICATIONS

Cantor et al., "The behavior of biological macromolecules." *Biophysical Chemistry, Part III*, 979-1039 (1980).

Capone, "Screening Recombinant Baculovirus Plaques In Situ with Antibody Probes," *Gene Anal. Techn.*, 6, 62-66 (1989).

Casey et al., "*Neisseria gonorrhoeae* Survive Intraleukocytic Oxygen—Independent Antimicrobial Capacities of Anaerobic and Aerobic Granulocytes in the Presence of Pyocin Lethal for Extracellular Gonococci", Infect. Immun.52:384-389 (1986).

Cody et al., "Protective Anti-lipopolysaccharide Monoclonal Antibodies Inhibit Tumor Necrosis Factor Production,", *J. Surg. Res.*, 52(4):314-319 (1992).

Dahlberg et al., "A Novel Endotoxin Antagonist Attenuates Tumor Necrosis Factor-$\alpha$ Secretion." *Journal of Surgical Research*, 63, 44-48 (1996).

D'Amato et al., "Thalidomide is an Inhibitor of Angiogenesis," *Proc. Natl. Acad. Sci. USA*, 91(9):4082-4085 (1994).

Dameron et al., "Control of Angiogenesis in Fibroblasts by p53 Regulation of Thrombospondin-1," *Science*, 265:1582-1584 (1994).

Deuel et al., "Amino acid sequence of human platelet factor 4," *Proc. Natl. Acad. Sci. USA*, 74, 2256-2258 (1977).

Dintzis et al., "A Comparison of the Immunogenicity of a Pair of Enantiomeric Proteins," *Proteins: Structure, Function, and Genetics*, 16(3), 306-308 (1993).

Dugas et al., *Bioorganic Chemistry*, Springer-Verlag, New York, NY (1981), Title Page, Copyright Page, Table of Contents, and pp. 54-92.

Dunn et al., "Efficacy of type-specific and cross-reactive murine monoclonal antibodies directed against endotoxin during experimental sepsis," *Surgery*, 98, 283-290 (1985).

Elsbach et al., "Bactericidal/permeability increasing protein and host defense against Gram-negative bacterial and endotoxin," *Curr. Opn. in Imm.*, 5(1), 103-107 (1993).

Farley et al., "Lipopolysaccharide Structure Determines Ionic and Hydrophobic Binding of a Cationic Antimicrobial Neutrophil Granule Protein," *Infect. Immun.*, 56, 1589-1592 (1988).

Folkman et al., "Antiogenesis." *J. Biol. Chem.*, 267, 10931-10934 (1992).

Folkman, "What is the Evidence that Tumors are Angiogenesis Dependent?," *Journal of the National Cancer Institute*, 82, 4-6 (1990).

Gabay et al., "Antibiotic proteins of human polymorphonuclear leukocytes," *PNAS USA*, 86, 5610-5614 (1989).

Gallin et al., "Recent Advances in Chronic Granulomatous Disease," *Ann. Int. Med.*, 99, 657-674 (1983).

Gazzano-Santoro et al., "High-Affinity Binding of the Bactericidal/Permeability-Increasing Protein and a Recombinant Amino-Terminal Fragment to the Lipid A Region of Lipopolysaccharide," *Infect. Immun.*, 60(11), 4754-4761 (1992).

Gibbs et al., "A PFG NMR Experiement for Accurate Diffusion and Flow Studies in the Presence of Eddy Currents", J. Magnetic Resonance, 93:395-402 (1991).

Gray et al., "Cloning of the cDNA of a Human Neutrophil Bactericidal Protein," *J. Biol. Chem.*, 264(16), 9505-9509 (1989).

Gray et al., Cystic Fibrosis Foundation Grant No. 2R01-Al-26159 awarded by NIH (1990) (Abstract Only).

Gray, "Metabolic Stimulation and Bactericidal Function of Polymorphonuclear Leukocytes," *J. Retic. Soc.*, 22(2):87-88 (1977).

Griffioen et al., "Endothelial Intercellular Adhesion Molecule-1 Expression Is Suppressed in Human Malignancies: The Role of Angiogenic Factors." *Cancer Research*, 56, 1111-1117 (1996).

Griffioen et al., "Anginex, a designed peptide that inhibits angiogenesis", (2001) *Biochemical Society*, 354, 233-242.

Griffioen et al., "Tumor Angiogenesis Is Accompanied by a Decreased Inflammatory Response of Tumor-Associated Endothelium," *Blood*, 88(2):667-673 (1996).

Griffioen et al., "Tumor Angiogenesis Is Accompanied by a Decreased Inflammatory Response of Tumor-Associated Endothelium," *Proc. Am. Ass. Cancer Res.*, 37:55, Abstract No. 380 (1996).

Groenewegen et al., "Supernatants of Human Leukocytes Contain Mediator, Different From Interferon $\gamma$. Which Induces Expression of MHC Class II Antigens," *J. Exp. Med.*, 164:131-143 (1986).

Gupta et al., "A potent inhibitor of endothelial cell proliferation is generated by proteolytic cleavage of the chemokine platelet factor 4," *PNAS USA*,92, 7799-7803 (1995).

Hancock, "Alterations in Outer Membrane Permeability." *Ann. Rev. Microbiol.*, 38, 237-264 (1984).

Harlow et al., Eds., *Antibodies: A Laboratory Manual*, Cold Spring Harbor Laboratory (1988), Title Page. Copyright Page. and Table of Contents.

Hartree, "Determination of Protein: A Modification of the Lowry Method That Gives a Linear Photometric Response." *Analytical Biochem.*, 48, 422-427 (1972).

Hendsch et al., "Do salt bridges stabilize proteins? A continuum electrostatic analysis." *Protein Science*, 3, 211-226 (1994).

Heumann et al., "Competition between Bactericidal/Permeability-Increasing Protein and Lipopolysaccharide-Binding Protein for Lipopolysaccharide Binding to Monocytes," *J. Infect. Dis.*, 167(6), 1351-1357 (1993).

Hoess et al., "Crystal structure of an endotoxin-neutralizing protein from the horseshoe crab. *Limulus* anti-LPS factor, at I 6 ø resolution." *EMBO J.*, 12(9), 3351-3356 (1993).

Holmes et al., "Studies of the metabolic Activity of Leukocytes from Patients with a Genetic Abnormality of Phagocytic Function". *J. Clin. Invest*, 46:1422-1432 (1976).

Holmes et al., "Fatal Granulomatous Disease of Childhood," *Lancet*, 1, 1225-1228 (1966).

Holmes. "Metabolic Stimulation and Bactericidal Function of Polymorphonuclear Leukocytes", Reticulo. Soc., 22:87-88 (1978).

Holt et al., "Biochemistry of $\alpha$ Granule Proteins," *Seminars in Hematology*, 22(2), 151-163 (1985).

Homma, "A New Antigenic Schema and Live-cell Slide-agglutination Procedure for the Infrasubspecific. Serologic Classification of *Pseudomonas aeruginosa,*" *Japan J. Exp. Med.*, 46,(6), 329-336 (1976).

Hovde et al., "Physiological Effects of a Bactericidal Protein from Human Polymorphonuclear Leukocytes on *Pseudomonas aeruginosa,*" *Infect. Immun.*, 52(1), 90-95 (1986).

Hovde et al., "Characterization of a Protein from Normal Human Polymorphonuclear Leukocytes with Bactericidal Activity against *Pseudomonas aeruginosa,*" *Infect. Immun.*, 54(1), 142-148 (1986).

Ilyina et al., "NMR Structure of a *de Novo* Designed. Peptide 33mer with Two Distinct. Compact $\beta$-Sheet Folds," *Biochemistry*, 36(17):5245-5250 (1997).

Ilyina et al., "Synthetic Peptides Probe Folding Initiation Sites in Platelet Factor-4: Stable Chain Reversal Found within the Hydrophobic Sequence LIATLKNGRKISL," *Biochemistry*, 33 13436-13444 (1994).

Ilyina et al., "Multiple native-like conformations trapped via self-association-induced hydrophobic collapse of the 33-residue β-Sheet domain from platelet factor 4." *Biochem. J.*, 306, 407-419 (1995).

Jameson et al., "A rationally designed CD4 analogue inhibitis experimental allergic encephalomyelitis," *Nature*, 368, 744-746 (1994).

Jeener et al., "Investigation of exchange processes by two-dimensional NMR spectroscopy," *J. Chem. Phys.*, 71(11), 4546-4553 (1979).

Johnston, Jr., et al., "Chronic Granulomatous Disease," *The Pediatric Clinics of North America*, 24(2), 365-376 (1977).

Johnston, "Molecular Science Sets Its Sights on Septic Shock," *J. NIH Res.*, 3(10), 61-65 (1991).

Kambic et al., "Biomaterials in Artificial Organs," *C& EN*, 64(2):30-48 (1986).

Kelly et al., "Role of bactericidal permeability—increasing protein in the treatment of gram-negative penumonia," *Surgery*, 114(2), 140-146 (1993).

Kim et al., "Thermodynamic β-sheet propensities measured using a zinc-finger host peptide,", *Nature*, 362, 267-270 (1993).

Kitayama et al., "Suppressive Effect of Basic Fibroblast Growth Factor on Transendothelial Emigration of CD4(+) T-lymphocyte," Cancer Res., 54 (17):4729-4733 (1994).

Kyte et al., "A Simple Method for Displaying the Hydropathic Character of a Protein." *J. Mol. Biol.*, 157, 105-132 (1982).

Lasdun et al., "Inhibition of Endopeptidase 24.15 Slows the *in Vivo* Degradation of Luteinizing Hormone-Releasing Hormone." *J. of Pharm. and Exp. Therapeutics*, 251(2), 439-447 (1989).

Lehrer et al., "Defensins: Antimicrobial and Cytotoxic Peptides of Mammalian Cells." *Annu. Rev. Immunol.*, 11, 105-28 (1993).

Little et al., "Functional Domains of Recombinant Bactericidal/Permeability Increasing Protein (rBPI$_{23}$)," *J. Biol. Chem.*, 269, 1865-1872 (1994).

Luckow et al., "Trends in the Development of Baculovirus Expression Vectors." *Bio/Technology. 6*, 47-55 (1988).

Luster et al., "The IP-10 Chemokine Binds to a Specific Cell Surface Heparan Sulfate Site Shared with Platelet Factor 4 and Inhibits Endothelial Cell Proliferation." *J. Exp. Med.*, 182, 219-231 (1995).

Mandell, "Bactericidal Activity of Aerobic and Anaerobic Polymorphonuclear Neutrophils." *Infect. Immun.*, 9(2), 337-341 (1974).

Mannion et al., "Separation of Sublethal and Lethal Effects of the Bactericidal/Permeability Increasing PRotein on *Escherichia coli,*" *J. Clin. Invest.*, 85, 853-860 (1990).

Marion et al., "Application of Phase Sensitive Two-Dimensional Correlated Spectroscopy (COSY) for Measurements of $^1$H-$^1$H Spin-Spin Coupling Constants in Proteins,", *Biochemical and Biophysical Research Communications,*, 113(3), 967-974 (1983).

Marra et al., "Bactericidal/Permeability-Increasing Protein has Endotoxin-Neutralizing Activity," *J. Immunol.*, 144(2). 662-666 (1990).

Marra et al., "The Role of Bactericidal/Permeability-Increasing Protein as a Natural Inhibitor of Bacterial Endoxtoxin," *J. Immunol.*, 148(2), 532-537 (1992).

Martinotti et al., "Heavy-metal Modulation of the Human Intercellular Adhesion Molecule (ICAM-I) Gene Expression," *BBA—Gene Structure and Expression*, 1261:107-114 (1995).

Mayer et al., "Declining Severity of First Attack of Rheumatic Fever." *Amer. J. Dis. Chil.*, 105, 146-152 (1963).

Mayo et al., "A recipe for designing water-soluble β-sheet-forming peptides." *Protein Science*, 5, 1305-1315 (1996).

Mayo et al. "Designed β-sheet-forming peptide 33mers with potent human bactericidal/permeability increasing protein-like bactericidal and endotoxin neutralizing activities", (1998) *Biochimica et Biophysica Acta 1425*, 81-92.

Mayo et al., "Structure-function relationships in novel peptide dodecamers with broad-spectrum bactericidal and endotoxin-neutralizing activities",(2000) *Biochem J*, 349, 717-728.

Mayo et al., "Designed β-sheet peptides that inhibit proliferation and induce apoptosis in endothelial cells" (2001) *Angiogenesis* 4(1), 45-51.

Mayo et al., "NMR Solution Structure of the 32-kDa Platelet Factor 4 ELR-Motif N-Terminal Chimera: A Symmetric Tetramer." *Biochemistry.* 34. 11399-11409 (1995).

McCloskey et al., "Treatment of Septic Shock with Human Monoclonal Antibody HA-1A." *Ann. Inter. Med.*121, 1-5 (1994).

Miller et al., "Biology and Biochemistry of the Chemokines: A Family of Chemotactic and Inflammatory Cytokines." *Critical Reviews in Immunology*, 12(1.2) 17-46 (1992).

Minor, Jr. et al., "Context is a major determinant of β-sheet propensity." *Nature*, 371, 264-267 (1994).

Minor, Jr. et al., "Measurement of the β-sheet-forming propensities of amino acids.", *Nature*, 367, 660-663 (1994).

Mossman, "Rapid Colorimetric Assay for Cellular Growth and Survival: Application to Proliferation and Cytotoxicity Assays," *Journal of Immunological Methods*, 65(1-2), 55-63 (1983).

Okamura et al., "Outer Membrane Mutants of *Salmonella typhimurium* LT2 Have Lipopolysaccharide-Dependent Resistance to the Bactericidal Activity of Anaerobic Human Neutrophils." *Infect. Immun.*, 36(3), 1086-1095 (1982).

Ooi et al., "A 25-kDa NH$_2$-terminal Fragment Carries All the Antibacterial Activities of the Human Neutrophil 60-kDa Bactericidal/Permeability-increasing Protein," *J. Biol. Chem.*, 262(31). 14891-14894 (1987).

Ooi et al., "Endotoxin-neutralizing Properties of the 25 kD N-Terminal Fragment and a Newly Isolated 30 kD C-Terminal Fragment of the 55-60 kD Bactericidal/Permeability-increasing Protein of Human Neutrophils." *J. Exp. Med.*, 174, 649-655 (1991).

O'Reilly et al., "Angiostatin: A Novel Angiogenesis Inhibitor That Mediates the Suppression of Metastases by a Lewis Lung Carcinoma," *Cell*, 79(2):315-328 (1994).

O'Reilly et al., "Endostatin: An Endogenous Inhibitor of Angiogenesis and Tumor Growth," *Cell*, 88(2):277-285 (1997).

Otzen et al., "Side-Chain Determinants of β-Sheet Stability, " *Biochemistry*, 34(17), 5718-5724 (1995).

Pereira et al., "Synthetic bactericidal peptide based on CAP37: A 37-kDa human neutrophil granule-associated cationic antimicrobial protein chemotactic for monocytes." *PNAS USA*, 90, 4733-4737 (1993).

Piali et al., "Endothelial Vascular Cell Adhesion and Carcinoma," J. Exp. Med. 181(2):811-816 (1995).

Piantini et al., "Multiple Quantum Filters for Elucidating NMR Coupling Networks." *J. Am. Chem. Soc.*, 104, 6800-6801 (1982).

Quie et al., "*In Vitro* Bactericidal Capacity of Human Polymorphonuclear Leukocytes: Diminished Activity in Chronic Granulomatous Disease of Childhood." *J. Clin. Invest.*, 46(4), 668-679 (1967).

Quinn et al., "Betadoublet: *De novo* design. synthesis. and characterization of a β-sandwich protein." *PNAS USA*, 91. 8747-8751 (1994).

Rest. "Killing of *Neisseria gonorrhoeae* by Human Polymorphonuclear Neutrophil Granule Extracts." Infect. Immun., 25(2), 574-579 (1979).

Rest et al., "Interactions of *Neisseria gonorrhoeae* with Human Neutrophils: Effects of Serum and Gonococcal Opacity on Phagocyte Killing and Chemiluminescence." *Infect. Immun.*, 36(2), 737-744 (1982).

Richardson et al., "The de novo design of protein structures. " *TIBS*, 14, 6 pp. (Jul. 1989).

Richardson et al., "Looking at proteins: representations, folding, packing, and design." *Biophysical Journal*, 63. 1186-1209 (1992).

Rustici et al., "Molecular Mapping and Detoxification of the Lipid A Binding Site by Synthetic Peptides," *Science*, 259, 361-365 (1993).

Sambrook et al., (Eds.), *Molecular Cloning: A Laboratory Manual, 2nd Edition*, Cold Spring Harbor Laboratory Press (1989), Title Page and Table of Contents.

Searle et al., "A short linear peptide derived from the N-terminal sequence of ubiquitin folds into a water-stable non-native β-hairpin." *Nature Structural Biology*, 2(11), 999-1006 (1995).

Shafer et al., "Lipid A and Resistance of *Salmonella typhimurium* to Antimicrobial Granule Proteins of Human Neutrophil Granulocytes." *Infect. Immun.*, 43(3). 834-838 (1984).

Shafer et al., "Cationic Antimicrobial Proteins from Human Neutrophil Granulocytes in the Presence of Diisopropyl Fluorophosphate." *Infect. Immun.*, 45(1), 29-35 (1984).

Shafer et al., "Synthetic Peptides of Human Lysosomal Cathespin G with Potent Antipseudomonal Activity." *Infect. Immun.*, 61(5). 1900-1908 (1993).

Shinefield et al., "Bacterial Interference: Its Effect on Nursery-Acquired Infection with *Staphylococcus aureus*." *Amer. J. Dis. Children*. 105:646. 1963.

Siefferman et al., "*Pseudomonas aeruginosa* Variants Isolated from Patients with Cystic Fibrosis are Killed by a Bactericidal Protein from Human Polymorphonuclear Leukocytes", Infect. Immun. 59:2152-2157 (1991).

Smith et al., "Guidelines for Protein Design: The Energetics of β Sheet Side Chain Interactions." Science, 270. 980-982 (1995).

Smith et al., "A Thermodynamic Scale for the β-Sheet Forming Tendencies of the Amino Acids." *Biochemistry*, 33, 5510-5517 (1994).

Spitznagel et al., "Antibiotic Proteins of Human Neutrophils." *J. Clin. Invest.*, 86(5). 1381-1386 (1990).

States et al., "A Two-Dimensional Nuclear Overhauser Experiment with Pure Absorption Phase in Four Quadrants," *J. Magnetic Resonance*, 48, 286-292 (1982).

Stewart et al., *Solid phase peptide synthesis*, 2nd ed. Rockford. Illinois, Pierce Chemical Co. pp. 125-135 (1984).

Su et al., "In Vitro Stability of Growth Hormone Releasing Factor (GRF) Analogs in Porcine Plasma." *Horm. Metab. Res.*, 23, 15-21 (1991).

Summers et al., *A Manual of Methods for Baculovirus Vectors and Insect Cell Culture Procedures*, Title Page, Copyright Page, and Table of Contents (1987).

Tanimura et al., "Determinants of protein side-chain packing," *Protein Science*, 3, 2358-2365 (1994).

Taraboletti et al., "Inhibition of Angiogenesis and Murine Hemangioma Growth by Batimastat, a Synthetic Inhibitor of Matrix Metalloproteinases." *J. Natl. Cancer. Inst.*, 87(4): 293-298 (1995).

Uknis et al., "Design of a Potent Novel Endotoxin Antagonist," *Surgery*, 122(2):380-385 (1997).

van der Shaft, et al. The Designer Antiangiogenic Peptide Anginex Targets Tumor Endothelial Cells and Inhibits Tumor Growth in Animal Models. *FASEB Journal* Express Article 10.1096/fj.02-0509fje. Published online Oct. 18, 2002.

Verma, "Improved Genomic Blot Hybridization." *Bio/Tech.*, 7, 934 (1989).

Wang et al., "Direct double-stranded DNA sequencing with baculovirus genomes," *J. Virol. Meth.*, 31, 113-118 (1991).

Wasiluk et al., "Comparison of Granule Proteins from Human Polymorphonuclear Leukocytes Which Are Bactericidal toward *Pseudomonas aeruginosa*," *Infect. Immun.*, 59(11), 4193-4200 (1991).

Weiss et al., "Purification and Characterization of a Potent Bactericidal and Membrane Active Protein from the Granules of Human Polymorphonuclear Leukocytes," *J. Biol. Chem.*, 253, 2664-2672 (1978).

Weiss et al., "Killing of Gram-Negative Bacteria by Polymorphonuclear Leukocytes." *J. Clin. Invest.*, 69, 959-970 (1982).

Weiss et al., "Role of Charge and Hydrophobic Interactions in the Action of the Bactericidal/Permeability-increasing Protein of Neutrophils on Gram-negative Bacteria", *J. Clin. Invest.*, 71(3), 540-549 (1983).

Weiss et al., "Environmental Modulation of Lipopolysaccharide Chain Length Alters the Sensitivity of *Escherichia coli* to the Neutrophil Bactericidal/Permeability-Increasing Protein," *Infect. Immun.*, 51(2), 594-599 (1986).

Weiss et al., "Human Bactericidal/Permeability-increasing Protein and a Recombinant $NH_2$-Terminal Fragment Cause Killing of Serum-resistant Gram-negative Bacterial in Whole Blood and Inhibit Tumor Necrosis Factor Release Induced by the Bacteria," *J. Clin. Invest.*, 90, 1122-1130 (1992).

Wills et al., "Concentration Dependence of the Diffusion Coefficient of a Dimerizing Protein: Bovine Pancreatic Trypsin Inhibitor," *J. Phys. Chem.*, 85, 3978-3984 (1981).

Wider et al., "Homonuclear Two-Dimensional $^1$H NMR of Proteins. Experimental Procedures." *J. Magnetic Resonance*. 56(2). 207-234 (1984).

Yan et al., "Engineering of betabellin 14D: Disulfide-induced folding of a β-sheet protein," *Protein Science*, 3, 1069-1073 (1994).

NATIVE α-CHEMOKINE SEQUENCES.

| | | | | | | | | | | | | | | | | | | | | | | | | | | |
|---|---|---|---|---|---|---|---|---|---|---|---|---|---|---|---|---|---|---|---|---|---|---|---|---|---|---|
| PF4 | R | H | I | T | S | L | E | V | I | K | A | G | P | H | S | P | T | A | Q | L | I | A | T | L | K | N | G | R | K | I | S | L | D |
| | | | | 25 | | | | | | 30 | | | | | 35 | | | | | 40 | | | | | 45 | | | | | 50 | | | |
| IL-8 | K | F | I | K | E | L | R | V | I | E | S | G | P | H | S | A | N | T | E | I | I | V | K | L | S | D | G | R | E | L | S | L | D |
| GRO | K | N | I | Q | S | V | N | V | K | S | P | G | P | H | S | A | Q | T | E | V | I | A | T | L | K | N | G | R | K | A | S | L | N |

DESIGNED PEPTIDES.

Fig. 1

SYNTHETIC APPROACH TO DESIGNED CHEMICAL STRUCTURES

This is a division of application Ser. No. 09/194,296, filed Oct. 15, 1999 now U.S. Pat. No. 6,486,125 which is a 371 of PCT/US97/08944, filed May 23, 1997, which is a Continuation-in-Part of Ser. No. 08/671,487, filed Jun. 27, 1996 (U.S. Pat. No. 5,955,577) and a Continuation-in-Part of Ser. No. 08/653,632, filed May 24, 1996 (U.S. Pat. No. 5,830,860), all incorporated herein by reference.

FIELD OF THE INVENTION

This invention relates to the fields of chemical design and to methods for selecting, modifying, and creating synthetic chemical structures and to their methods of use.

BACKGROUND

A critical feature of a polypeptide is its ability to fold into a three dimensional conformation or structure. Polypeptides usually have a unique conformation which, in turn, determines their function. The conformation of a polypeptide has several levels of structure. The primary structure is a linear sequence of a series of amino acids linked into a polypeptide chain. The secondary structure describes the path that the polypeptide backbone of the polypeptide follows in space, and the tertiary structure describes the three dimensional organization of all the atoms in the polypeptide chain, including the side groups as well as the polypeptide backbone.

Covalent and noncovalent interactions between amino acids determine the conformation of a polypeptide. The most common covalent bond used in establishing the secondary and tertiary structure of a polypeptide is the formation of disulfide bridges between two cysteine residues (forming cysteine). The formation of noncovalent bonds is influenced by the aqueous environment such as water. A large number of noncovalent interactions, such as van der Waals, ionic, hydrophobic and hydrogen-bonded interactions, contribute to the way in which a polypeptide folds. Hydrophobic interactions, which occur between amino acids with nonpolar side chains, are particularly important because they associate to exclude water. These side chains generally form the core of the polypeptide, where they are mostly inaccessible to water.

The secondary structure of polypeptides can be divided into two general classes: α-helix and β-sheet. An α-helix is stabilized by hydrogen bonding and side chain interactions between amino acids three and four residues apart in the same polypeptide chain, whereas a β-sheet is stabilized by hydrogen bonding and side chain interactions between amino acids more distant in a polypeptide chain and in different polypeptide chains. A complete understanding of the construction of α helices and β sheets is important for the manipulation of the structure and function of polypeptides.

A major challenge in de novo polypeptide design (more often referred to as de novo peptide design), which is the design of polypeptides (or peptides) from scratch, is the engineering of a polypeptide having the folding stability of the native structure of a natural polypeptide. Several polypeptides have been designed with the α helix as the major structural element. Few polypeptides have been designed with the β sheet as the major structural element. Unlike α helices where there is a regular succession of hydrogen bonds between amides three and four residues apart in the sequence, β sheets are formed by residues at variable and often distant positions in the sequence. In addition, they tend to form aggregates in solution and precipitate under physiological conditions. A major difficulty in designing a structurally stable β polypeptide is dealing with the interactions between β sheets.

Designing a polypeptide to form a β-sheet has in the past usually been based on one of a number of structural propensity scales known in the art. These scales are derived either statistically from structural databases of known folded polypeptides or by making single or minimal site-specific changes in a fully folded polypeptide. See, for example, C. A. Kim, et al., *Nature,* 362, 267 (1993); D. L. Minor, et al., *Nature,* 371, 264 (1994); D. L. Minor, et al., *Nature,* 367, 660 (1994); and C. K. Smith, et al., *Biochemistry,* 33, 5510 (1994). However, such scales are generally less useful when designing de novo β-sheet folds in short peptides where considerably more β-sheet and/or side-chain surface (particularly hydrophobic surface) will be exposed to water. D. E. Otzen, et al., *Biochemistry,* 34, 5718 (1995).

Betabellin was one of the first de novo designed class of β-sheet peptides. J. Richardson, et al., *Biophys. J.,* 63, 1186 (1992). It was intended to fold into a sandwich of two identical four-stranded, antiparallel β sheets. A more recent version of betabellin, betabellin 14D, was designed by Yan, et al., *Protein Science,* 3, 1069, (1994). Quinn, et al. designed betadoublet, which is similar to betabellin but contains only naturally encoded amino acids. T. P. Quinn, et al., *Proc. Natl. Acad. Sci. U.S.A.,* 91, 8747 (1994).

However, peptides in the betabellin and betadoublet series show limited solubility in water and minimal, highly transient β-sheet structure, i.e., nonstable structures. The best betabellin made thus far, Betabellin peptide 14D, for example, becomes less soluble at pH values above 5.5 making it impractical for use at a physiological pH. Moreover the β-sheet structure formed by peptide 14D relies on the presence of an intermolecular disulfide bridge to yield a dimeric species. The peptides of the present invention do not have these limitations. Betadoublet, which has the same predicted antiparallel β-sheet motif as betabellin, is even less water soluble, and only at a lower pH of about 4, and fails to show any compact, stable folding, i.e., structure.

Water solubility and pH ranges are important to peptide function. A polypeptide that is not soluble under physiological conditions (i.e., in water at a pH of about 7.0–7.4 and in about 150 mM NaCl or an equivalent physiological salt) is not functional and is therefore not useful. Neither the betabellin nor the betadoublet strategies for peptide design achieved sufficient solubility, peptide compactness, or peptide self-association under physiological conditions.

Hence, there remains a need for β-sheet forming peptides that are not only water soluble, but soluble at physiological conditions, and self associate.

Sepsis syndrome continues to be one of the leading causes of mortality in critically ill patients and gram-negative bacterial pathogens cause about ⅓ of these cases. Despite intensive laboratory and clinical investigation, the mortality associated with gram-negative bacterial sepsis and shock remains at about 40%, a statistic that has changed little over time. Lipopolysaccharide (LPS, or endotoxin) is an integral component of the outer membrane of gram-negative bacteria and triggers activation of macrophages that, in turn synthesize and secrete cytokines within the endogenous tissue milieu and systemic circulation. The resultant release of tumor necrosis factor-α (TNF-α) and other cytokines by macrophages is causally linked to the host inflammatory response and the subsequent development of septic shock. Unfortunately, standard inflammatory response and the subsequent development of sepsis and shock, including administration of potent antibiotics, aggressive fluid resuscitation, hemodynamic monitoring, and metabolic support, has not been associated with a significant reduction in mortality.

A 27 amino acid synthetic peptide based on amino acids 82–108 of BPI significantly inhibited TNF-α secretion in vitro and administration of the peptide in animal models diminished endotoxin levels, although abrogation of TNF-α secretion was incomplete (Battafarano et al. *Surgery* 118: 318–324, 1995 and Dahlberg, et al. *J. Surg. Res.* 63:44–48, 1996). The effect of anti-endotoxin monoclonal antibodies HA-1A and E5 on mortality during sepsis syndrome has been studied by phase III clinical trial. In these studies, mortality rates were not reduced as compared to placebo treatments (The CHESS trial study group, *Ann. Int. Med.* 121:1–5, 1994; Bone et al. *Crit. Care Med.* 23:994–1005, 1995). Accordingly, novel reagents are needed to treat gram-negative bacterial infections.

Tumor growth can be controlled by deprivation of vascularization (see Folkman, *Natl. Cancer. Inst.* 82:, 4–6, 1990 and Folkman et al. *J. Biol. Chem.* 267:10931–10934, 1992). A growing number of endogenous inhibitors of angiogenesis include platelet factor-4 (PF4, Gupta et al. *Proc. Natl. Acad. Sci. USA* 92:7799–7803, 1995), interferon-γ inducible protein-10 (IP-10, Luster, et al. *J. Exp. Med.* 182:219–231, 1995), as well as synthetic agents including thalidomide, metalloproteinase inhibitors, and the like. There is a need for reagents to inhibit angiogenesis including agents that inhibit endothelial cell proliferation for a variety of applications, including, but not limited to tumorigenesis.

SUMMARY OF THE INVENTION

The present invention provides a method for synthesizing a water-soluble peptide having at least about 35% amino acids having hydrophobic side chains, the method comprising combining amino acids having charged side chains and amino acids having noncharged polar side chains with amino acids having hydrophobic side chains, wherein the amino acids having charged side chains are provided in a ratio of at least about 2:1 amino acids having positively charged side chains to amino acids having negatively charged side chains.

The present invention also provides a method for synthesizing a water-soluble peptide having at least about 35% amino acids having hydrophobic side chains, the method comprising combining amino acids having charged side chains and less than about 20% amino acids having noncharged polar side chains with amino acids having hydrophobic side chains, wherein: the amino acids having charged side chains are provided in a ratio of at least about 2:1 amino acids having positively charged side chains to amino acids having negatively charged side chains; the water-soluble peptide has about 35% to about 55% amino acids having hydrophobic side chains; and at least two of the amino acids having hydrophobic side chains are positioned in the peptide with an intervening turn sequence in a manner such that the two amino acids having hydrophobic side chains are capable of aligning in a pairwise fashion to form a β-sheet structure; and the turn sequence is LXXGR, wherein each X is independently selected from the group consisting of K, N, S, and D. Herein, percentages are reported as the number of specified amino acids relative to the total number of amino acids in the peptide chain.

This invention also relates to a series of βpep peptides prepared using the methods of this invention. These peptides are provided as βpep-1 through βpep-30 and correspond to SEQ ID NO:1 through SEQ ID NO:30. This invention also relates to a method for treating a bacterial infection or endotoxic shock comprising administering an amount of a pharmaceutical composition effective to inhibit the bacterial infection or neutralize endotoxin to a mammal, wherein the pharmacutical composition comprises (a) a peptide demonstrating bactericidal activity or endotoxin neutralizing activity selected from the group consisting of βpep-1 through βpep30 (SEQ ID NO: 1 through SEQ ID NO:30); and (b) a pharmaceutically acceptable carrier.

In one embodiment, the peptide neutralizes endotoxin, in another the peptide is bactericidal and in another the peptide is both bactericidal and neutralizes endotoxin. In a preferred embodiment, the peptide has endotoxin neutralizing acitivity and is selected from the group consisting of βpep-8 and βpep-23. In another preferred embodiment, the peptide has bactericidal activity and is selected from the group consisting of βpep-19, βpep-7, βpep-4, βpep-22 and βpep-1.

This invention also relates to a method for inhibiting TNF-α levels in a mammal comprising the step of administering a therapeutically effective amount of a pharmaceutical composition comprising: (a) a peptide demonstrating bactericidal activity or endotoxin neutralizing activity selected from the group consisting of βpep-1 through βpep30 (SEQ ID NO: 1 through SEQ ID NO:30); and (b) a pharmaceutically acceptable carrier. In a preferred embodiment the peptide is βpep-3.

This invention also relates to a method for inhibiting endothelial cell proliferation comprising the step of administering an effective amount of a composition comprising: a peptide demonstrating endothelial cell proliferation inhibition selected from the group consisting of βpep-1 through β-pep-30 (SEQ ID NO: 1 through SEQ ID NO:30). In one embodiment, the composition is a therapeutically effective amount of a pharmaceutical composition comprising: a peptide selected from the group consisting of βpep-14 or βpep-16; and a pharmaceutically acceptable carrier.

The invention also relates to a method for promoting inter-cellular adhesion molecule (ICAM) expression comprising the step of administering an effective amount of a composition comprising: a peptide promoting inter-cellular adhesion molecule expression selected from the group consisting of βpep-1 through βpep-30 (SEQ ID NO:1 through SEQ ID NO:30).

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted. One letter and three letter symbols are used herein to designate the naturally occurring amino acids. Such designations including R or Arg, for Arginine, K or Lys, for Lysine, G or Gly, for Glycine, and X for an undetermined amino acid, and the like, are well known to those skilled in the art.

The term "peptide" or "polypeptide" is used herein to refer to an amino acid polymer. A single peptide of this invention preferably has at least 20 amino acids. Preferably the peptides of this invention are no greater than 50 amino acids in length, and more preferably about 28 to about 33 amino acids in length.

The term "water-soluble" is used herein to refer to compounds, molecules, and the like, including the peptides of this invention, that are preferably readily dissolved in water. The compounds of this invention are readily dissolved in water if about 1 mg of the compound dissolves in 1 ml of water having a temperature of about 35–45° C. More preferably, the peptides of this invention will have a water solubility of at least about 10 mg/ml and often of at least about 20 mg/ml. Even more preferably, the peptides are soluble at these concentrations under physiological conditions, including a pH of about 7.0–7.4 and a salt concentration of about 150 mM NaCl.

The term "hydrophobic amino acid side chain" or "nonpolar amino acid side chain," is used herein to refer to amino acid side chains having properties similar to oil or wax in that they repel water. In water, these amino acid side chains interact with one another to generate a nonaqueous environment. Examples of amino acids with hydrophobic side chains include, but are not limited to, valine, leucine, isoleucine, phenylalanine, and tyrosine.

The term "polar amino acid side chain" is used herein to refer to groups that attract water or are readily soluble in water or form hydrogen bonds in water. Examples of polar amino acid side chains include hydroxyl, amine, guanidinium, amide, and carboxylate groups. Polar amino acid side chains can be charged or noncharged.

The term "noncharged polar amino acid side chain" or "neutral polar amino acid side chain" is used herein to refer to amino acid side chains that are not ionizable or do not carry an overall positive or negative charge. Examples of amino acids with noncharged polar or neutral polar side chains includes serine, threonine, glutamine, and the like.

The term "positively charged amino acid side chain" refers to amino acid side chains that are able to carry a full or positive charge and the term "negatively charged amino acid side chain" refers to amino acid side chains that are able to carry a negative charge. Examples of amino acids with positively charged side chains include arginine, histadine, lysine, and the like. Examples of amino acids with negatively charged side chains include aspartic acid and glutamic acid, and the like.

The term "self-association" refers to the spontaneous association of two or more individual peptide chains or molecules irrespective of whether or not the peptide chains are identical.

BRIEF DESCRIPTION OF THE FIGURES

FIG. 1 provides the alignment of β-sheet regions from the polypeptides PF4 (SEQ ID NO:36), IL-8 (SEQ ID NO:37) and GRO (SEQ ID NO:38) polypeptides. β-sheet residues are blocked-in and lines connect the residues that are paired in the chain. The C-termini in the sequences were synthesized in the amide form. Numbering shown below the PF4 sequence (SEQ ID NO:36) is that from native PF4.

FIG. 7A provides $^3$H-Thymidine incorporation data for FBHEC cells and FIG. 7B provides $^3$H-Thymidine incorporation data for HUVEC cells.

DETAILED DESCRIPTION OF THE INVENTION

Figure 2:
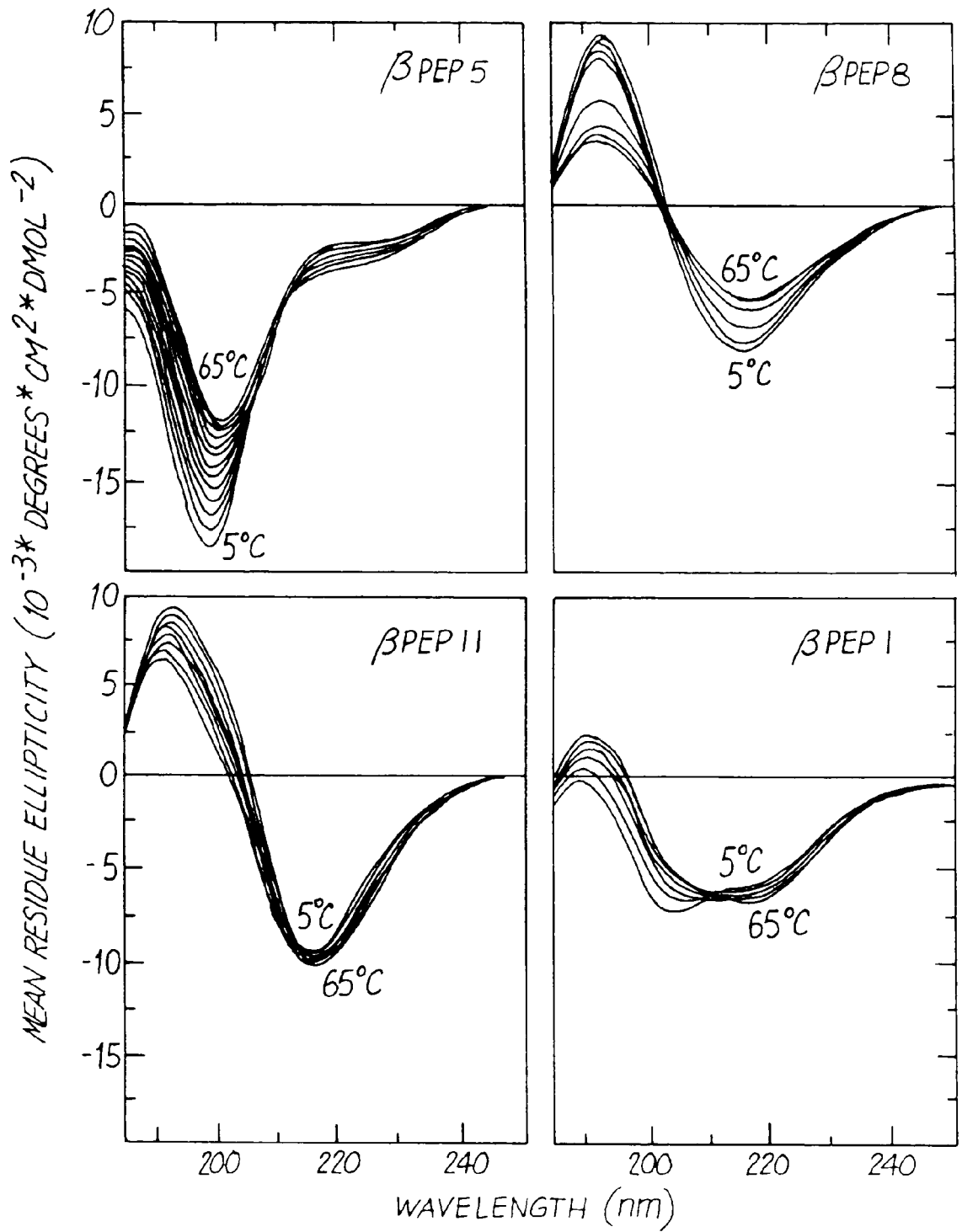
FIG. 2 is a graph illustrating the far-ultraviolet circular dichroic spectra for designed peptides βpep-5, βpep-8, βpep-11 and βpep-1. Peptide concentration used was 10 to 20 μM in 20 mM potassium phosphate, pH=6.3. The temperature was varied from 5° C. to 75° C.

An intricate interplay exists between peptide β-sheet formation, self-association, and water solubility. A challenge in making a soluble folded peptide is that solubility has a double-edged effect: precipitation versus over-solvation. Precipitation is the falling out of solution of a peptide, while over-solvation is the tendency of a soluble peptide to prefer intermolecular water-peptide interactions over intramolecular folding interactions. Going too far in either direction (precipitation or over-solvation) destabilizes the folded state. Reduced solubility generally occurs due to intermolecular peptide-to-peptide interactions (hydrophobic and electrostatic) which results in precipitation or gelation. Although the precipitate, for example, is in equilibrium with soluble peptide, the equilibrium is shifted away from solution. If a designed β-sheet-forming peptide contains a relatively large number of amino acids with hydrophobic side chains which are not screened to some extent by the folding process, precipitation or gelation may result. Inherent in the design of β-sheet forming peptides, therefore, is the capacity to self-associate, thereby screening hydrophobic surface from solvent water.

The present invention provides a method for the de novo design of peptides that are water soluble at or near physiological conditions and preferably form β-sheet structures. Preferably and advantageously, the water-soluble peptide forms, through self-association, a β-sheet in the absence of any intermolecular covalent interactions (although this is not necessarily a requirement). The method takes into account the following parameters: the number or percentage composition of amino acids with positively and negatively charged side chains, the number or percentage composition of amino acids with noncharged polar side chains, the number or percentage composition of amino acids with hydrophobic side chains, proper placement and pairing of amino acids in the sequence and in space, and specific turn character. The specific turn character refers to the composition of side chains of the amino acids positioned in the turn sequence. A turn sequence refers to a sequence of amino acids that reverses the direction of the amino acid sequence in space.

When the number of amino acids with positively and negatively charged side chains is about equal, intermolecular electrostatic interactions shift the solvation-precipitation equilibrium to the precipitate state. This was a fundamental flaw in previous design approaches. Adjusting the overall net charge of the peptide to mostly amino acids with positively charged side chains greatly improves solubility. Inter-peptide charge repulsion may also help to reduce precipitation. In a preferred embodiment of this invention, the ratio of amino acids with positively charged side chains to amino acids with negatively charged side chains is at least about 2:1. Preferably the ratio of amino acids with positively charged side chains to amino acids with negatively charged side chains is no greater than about 3:1; however, this invention also considers larger ratios of amino acids with positively charged side chains to amino acids with negatively charged side chains including, but not limited to 4:1, 5:1, 6:1 or greater.

The other side to solubility is that a peptide can be too soluble, i.e., over-solvated. When the number of amino acids with polar side chains is too high and other stabilizing forces are too low, intramolecular collapse or folding may be opposed by intermolecular peptide-water associations. Therefore, a high content of amino acids with short chain polar side chains such as serine and threonine (the hydroxylated amino acids) is not desirable, even though threonine is at the top of β-sheet propensity scales. This was another fundamental flaw in previous design approaches. The peptides of the present invention preferably contain less than 100%, preferably less than about 50%, more preferably, less than about 20% amino acids with noncharged polar side chains.

An appropriate percent composition of amino acids with hydrophobic side chains and proper placement in the sequence of such amino acids promotes self-association-induced structural collapse and stability. The trade-off is to adjust the percent composition of amino acids with hydrophobic side chains to avoid insolubility, while promoting folding and structure formation. The peptides of this invention preferably contain about 35% to about 55% amino acids with hydrophobic side chains, and in particularly preferred embodiments, about 40% to about 50% amino acids with hydrophobic side chains. In preferred embodiments of this invention, the hydrophobic amino acids, or combination thereof, are aliphatic, although aromatic hydrophobic amino acids are also possible.

To generate a more compact fold, side-chain pairing and packing must be optimized. Hydrophobic interactions increase folded state stability. Choosing the proper placement of amino acids with hydrophobic side chains in the sequence and combination of hydrophobic side-chain triplets across the strands as well as between strands in the self-associated peptide is an important feature to designing stable β-sheet folds. As used herein, a strand is that portion of a folded peptide chain between turn sequences.

Preferably, the amino acids are spacially positioned in the folded peptide to form a substantially hydrophobic surface. More preferably, the amino acids are spacially positioned in the folded peptide such that one peptide molecule is capable of self-associating with another peptide molecule to form a multimer.

The added dimension to this β-sheet design process is oligomerization where efficient hydrophobic side-chain packing of one sheet on top of another appears to be important for optimum folding stability and compactness. Choosing the proper placement of side chains, particularly hydrophobic side chains, in the amino acid sequence is important to controlling fold stability. Compact β-sheet folding is typically dependent on well-packed inter-strand side chain pairings. In a preferred embodiment of this invention at least two amino acids with hydrophobic side chains, and more preferably, three amino acids with hydrophobic side chains are positioned to align in space to form a β-sheet structure. Between these amino acids are turn sequences to allow for these side chain pairings.

Specific turn character may promote or stabilize a desired fold. A variety of turn sequences are known in the art. For a particular β-sheet fold, some turns may be important, while others may not. Those skilled in the art will be able to incorporate a turn sequence into the peptides designed according to the methods of this invention to test whether or not the peptide maintains a β-sheet structure, and the like, following the methods provided in the Examples that follow. A specific novel folding initiation turn/loop sequence, KXXGR (Ilyina et al., *Biochemistry* 33. 13436 (1994) was used in SEQ ID NOS:1–4 (βpep-5, βpep-8, βpep-11 and βpep-1), as described in the Example section of this disclosure. In this sequence, each X is independently selected from the group consisting of K, N, S, and D. This sequence was positioned between two amino acids with hydrophobic side chains such that the two amino acids having hydrophobic side chains were capable of aligning in a pairwise fashion to form a β-sheet structure.

Using the invention disclosed herein, 30 peptides, βpep-1 through βpep-30, were designed de novo (see Table 1, below). All βpep peptides are water soluble at least up to 30 mg/mL (9 mM) at pH values between pH=2 and pH=10, and all form β-sheets and have been shown by circular dichoism (CD) and nuclear magnetic resonance (NMR) to form significant populations of self-association-induced β-sheet structure in water at near-physiological conditions. βpep-1, in particular, exemplifies an exceptional application of this design approach by showing relatively stable, compact triple-stranded β-sheet structure with good side-chain packing. Others which behave similarly are βpep14 through βpep-30.

Using the methods of this invention it is possible to create any number of peptides, preferably peptides having β-sheet structure. This invention provides a method for designing a peptide scaffold to support a peptide in its native β-sheet structure. Those skilled in the art will recognize that there are a variety of proteins and polypeptides with β-sheet structures and that many of the proteins and polypeptides containing these β-sheet structures are known to mediate, promote or inhibit a variety of biological effects.

For example, a number of biological effects have been mapped to peptide sequences in a protein that exhibit β-sheet conformations. This invention permits the selection of a peptide sequence from a protein in a domain having β-sheet structure and the incorporation of this peptide sequence into a scaffold, according to this invention, to create a peptide with retained β-sheet structure. These novel peptides can have the same or improved biological activity that is attributed to the peptide domain while in the native protein with the advantage that the remaining portions of the protein are not required for activity. The use of an entire protein to duplicate the effect of a peptide domain complicates experimentation and therapy. Other domains in a protein may stimulate other biological and chemical effects including, but not limited to, enhanced antigenicity, decreased solubility, or stimulate unwanted biological responses, and the like. The protein is often labile or is not suited for biological or therapeutic applications without further modification. The strategy of this invention permits a functional peptide domain to be retained in its tertiary conformation within the scaffold of this invention. The methods of this invention provide direction for those skilled in the art to generate a variety of peptides with novel activities or with activities attributable to a parent protein from which the peptide was originally derived.

Peptides once prepared using the methods of this invention can be further modified in a variety of ways to form derivatives or analogs. These modifications include addition, substitution or deletion of amino acids either before the peptides are tested for biological activity or after testing the peptides for activity. Amino acid substitutions preferably do not eliminate the biological activity of the peptide. Conservative amino acid substations typically can be made without affecting biological activity. Conservative amino acid substitutions include substitution of an amino acid for another amino acid of the same type. Types of amino acids include: (1) basic amino acids such as lysine, arginine, and histidine; (2) hydrophobic amino acids such as leucine, isoleucine, valine, phenylalanine, and tryptophan; (3) non-polar amino acids including alanine, valine, leucine, isoleucine, proline, and methionine; (4) polar amino acids such as serine, threonine, cysteine, tyrosine, asparagine and glutamine; and (5) positively charged amino acids such as aspartic and glutamic acid.

The peptides prepared and designed according to this invention can be administered alone in a pharmaceutically acceptable buffer, as an antigen in association with another protein, such as an immunostimulatory protein or with a protein carrier such as, but not limited to, keyhole limpet hemocyanin (KLH), bovine serum albumin (BSA), ovalbumin, or the like. Peptides can be conjugated to other protein using standard methods such as activation of the carrier molecule with a heterobifunctional sulfosuccinimidyl 4-(n-maleimidomethyl) cyclohexane-1-carboxylate reagent. Cross-linking of activated carrier to a peptide can occur by reaction of the maleimide group of the carrier with the sulfhydryl group of a peptide containing a cysteine residue. Conjugates can be separated from free peptide through the use of gel filtration column chromatography or other methods known in the art.

The peptides with demonstrated biological activity can be administered to a mammal in an amount alone or together with other active agents and with a pharmaceutically acceptable buffer. For example, the peptides prepared according to this invention that demonstrate endotoxin neutralizing activity and/or bactericidal activity can be administered to treat a bacterial infection. The pharmaceutical composition can include a bactericidal peptide and/or an endotoxin neutralizing peptide prepared according to this invention. The peptides can be combined with a variety of physiological acceptable carriers for delivery to a patient including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide can be used. Other suitable carriers include, but are not limited to alcohol, phosphate buffered saline and other balances salt solutions.

The peptides prepared according to this invention that demonstrate biological activity can be administered in a variety of ways, including intravenously topically, orally and intramuscularly to a variety of mammals, including humans, mice and rabbits. The peptides can be administered as a single dose or in multiple doses. Preferably the dose is an effective amount as determine by the standard methods described herein and includes about 1 microgram to about 1,000 micrograms pretreatment, more preferably about 50 to about 250 micrograms pretreatment and those skilled in the art of clinical trials will be able to optimize dosages of particular peptides through standard trial studies.

The effective amount of a peptide for treating a bacterial infection will depend on the bacterial infection, the location of the infection and the peptide. An effective amount of the peptide is that amount that diminishes the number of bacteria in the animal and that diminishes the symptoms associated with bacterial infection such as fever, pain and other associated symptoms of the bacterial infection. The effective amount of a peptide can be determined by standard dose response methods in vitro and an amount of peptide that is effective to kill at least about 50 to 100% of the bacteria ($LD_{50}$) and more preferably about 60 to 100% of the bacteria would be considered an effective amount.

Alternatively, an effective amount of the peptide for treating a bacterial infection can be determined in an animal system such as a mouse. Acute peritonitis can be induced in mice such as outbred Swiss webster mice by intraperitoneal injection with bacteria such as *P. aeruginosa* as described by Dunn et al.(*Surgery*, 98:283, 1985); Cody et al. (*Int. Surg. Res.*, 52:315, 1992). Different amounts of peptide can be injected at one hour intravenously prior to the injection of the bacteria. The percentage of viable bacteria in blood, spleen and liver can be determined in the presence and absence of the peptide or other antibiotics. While not meant to limit the invention, it is believed that bactericidal peptide could also enhance the effectiveness of other antibiotics such as erythromycin, and the like.

Peptides with endotoxin neutralizing activity can be used to treat mammals infected with gram-negative bacteria systemically and that exhibit symptoms of endotoxin shock such as fever, shock and TNF-α release. The animals are typically infected with one or more gram-negative bacteria such as *Pseudomonas* spp., rough strains of *E. coli*, encapsulated *E. coli* and smooth strain *E. coli*. The endotoxin neutralizing peptide can be combined with other agents that are known and used to treat endotoxin shock.

A number of exemplary peptides were designed according to the methods of this invention (βpep-1 through βpep-30) and the peptides were synthesized according to Example 1. A number of these peptides appear to have a variety of biological applications. In one example, a number of peptides prepared according to this invention had endotoxin neutralizing activity, bactericidal activity or both endotoxin neutralizing activity and bactericidal activity.

A number of the peptides demonstrated endotoxin neutralizing activity, as compared to PF4 (see FIG. 1), and had improved activity as compared to an equivalent region from protein B/PI (amino acids 86–108). Results of these studies are provided in Example 5, Example 6 and including FIGS. 5 and 6. Domains within amino acids 86–108 of B/PI have been shown to have endotoxin neutralizing activity and the results from the studies indicated that a number of β peptides had endotoxin neutralizing activity. Endotoxin neutralizing activity can be measure by determining the molar concentration at which the peptide completely inhibits the action of lipopolysaccharide in an assay such as the *Limulus* amoebocyte lysate assay (LAL, Sigma Chemicals, St. Louis, Mo.) or the chromogenic LAL 1000 test (Biowhittacker, Walkersville, Md.). Endotoxin neutralizing activity can also be measured by calculating an inhibitory dose 50 ($LD_{50}$) using standard dose response methods. An inhibitory dose 50 is that amount of peptide that can inhibit 50% of the activity of endotoxin. Endotoxin activity can also be measured by determining the amount of release of tumor necrosis factor alpha (TNF-α) from a macrophage cell line or by evaluating the symptoms of shock in animals. Production of TNF-α can be assayed as described by Mossman et al.(*Immunological Methods* 65:55, 1983). Peptides preferably neutralized endotoxin at a molar concentration of about $1 \times 10^{-4}$ M to about $10^{-8}$M, more preferably about $10^{-5}$M to about $10^{-6}$M. Peptides were considered to not have endotoxin neutralizing activity did not neutralize endotoxin at a molar concentration of $10^{-4}$ or less.

Peptides having biological activity have a size about 10 amino acids to about 100 amino acids, more preferably about 10 to about 50 amino acids. Peptides with about 20 to about 50 amino acids are preferred and peptides of 28–33 amino acids are particularly preferred.

A number of the peptides prepared by this invention had bactericidal activity. Bactericidal activity can be evaluated against a variety of bacteria, preferably gram negative bacteria, but the types of bacteria can include *Pseudomonas* spp including *P. aeruginosa* and *P. cepacia*, *E. coli* strains, including *E. coli* B, *Salmonella*, *Proteus mirabilis* and *Staphylococcus* strains such as *Staphylococcus aureus*. A preferred organism is *Pseudomonas aeruginosa*. Bactericidal activity is determined by identifying the effective dose for killing as the molar concentration of the peptide which results in at least a 60% killing of the bacteria, as determined by standard methods. Preferably, the peptide has an effective dose at a concentration of about $1 \times 10^{-4}$M to about $1 \times 10^{-10}$M, and more preferably $1 \times 10^{-7}$M to about $1 \times 10^{-9}$M. Peptides that were not considered to be bactericidal did not kill *P. aeruginosa* at concentrations of $10^{-4}$M or less at a pH of 5.6. Bactericidal activity can also be determined by calculating a lethal dose 50 ($LD_{50}$) using standard methods. The $LD_{50}$ is that amount of peptide or protein that kills 50% of the bacteria when measured using standard dose response methods. A bactericidal peptide preferably has an $LD_{50}$ of about $10^{-4}$ M to about $10^{-9}$ M, more preferably about $10^{-7}$ M to about $10^{-9}$M.

In view of these results, this invention also relates to the use of peptides generated according to the methods of this invention to demonstrate bactericidal and/or endotoxin neutralizing activity. At least one of the peptides was also able to neutralize the effects of TNF-α in vivo.

In addition, some of the peptides prepared according to the methods of this invention are capable of inhibiting angiogenesis and/or endothelial cell proliferation. Example 8 provides methods for testing the angiogenesis or endothelial proliferation inhibiting capacity of peptides prepared according to the methods of this invention. In a preferred embodiment, βpep-4 was found to fold compactly and its NMR solution structure comprised two differently aligned, six stranded anti-parallel β-sheet dimer amphipaths sandwiched to form a tetramer. The βpep-4 β-sheet sandwich tetramer has a highly positively charged surface which makes it and other βpep peptides (Mayo et al. *Protein Sci* 5:1301–1315, 1996) good candidates for binding to anionic biomolecules like heparin and cell surface heparin sulfate and possibly for modulating various cellular activities. PF4 and other α-chemokines on which the βpep design was based, also have a relatively high net positive surface charge, bind to polysulfated glycosaminoglycans like heparin and trigger various cellular activities. Indeed, βpep-4 and related homologs may be novel chemokines. For this reason, a library of βpep peptide 33 mers, along with parent PF4, was screened for anti-angiogenic and related activites as provided in Example 8.

The methods of this invention relate to the use of effective amounts of the peptides prepared according to this invention to treat bacterial infection, endotoxic shock, mediate the effect of TNF-α (Example 7), inhibit endothelial cell proliferation and upregulate ICAM expression (Example 8). The compositions comprising, the peptides of this invention can be added to cells in culture or used to treat mammals. Where the peptides are used to treat mammals, the peptide is combined in a pharmaceutical composition comprising a pharmaceutically acceptable carrier such as a larger molecule to promote peptide stability or a pharmaceutically acceptable buffer that serves as a carrier for the peptide.

The invention will be further described by reference to the following detailed examples. These examples are offered to further illustrate the various specific and preferred embodiments and techniques. It should be understood, however, that many variations and modifications may be made while remaining within the scope of the present invention.

EXAMPLE 1

The Design and Synthesis of Water-Soluble β-Sheet Forming Peptides

Peptides of 33 amino acid residues in length, were synthesized on a Milligen Biosearch 9600 automated peptide synthesizer. The procedures used were based on Merrifield solid phase synthesis utilizing Fmoc-BOP chemistry (Stewart et al., 1984. *Solid phase peptide synthesis.*, 2nd ed. Rockford, Ill., Pierce Chemical Co. pp. 125–135). After the sequence had been obtained, the peptide support and side chain protection groups were acid cleaved (trifluoroacetic acid and scavanger mixture). Crude peptides were analyzed for purity on a Hewlett-Packard 1090M analytical HPLC using a reverse phase C18 VyDac column. Peptides generally were about 90% pure. Further purification was done on a preparative reverse-phase HPLC C-18 column using an elution gradient of 0–60% acetonitrile with 0.1% trifluoroacetic acid in water. Peptides then were analyzed for amino acid composition on a Beckman 6300 amino acid analyzer by total hydrolysis of samples using 6N HCl at 110° C. for 18–20 hrs. N-terminal sequencing confirmed peptide purity. The amino acid sequences and compositions of the four peptides are given in Table 1, and the composition of the peptides is provided in Table 2. βpep-11 contains an amino acid in the D configuration as represented by the superscripted D.

TABLE 1

| Amino Acid Sequence of β-Peptides |
|---|
| βpep-5 |
| KFIVTLRVIKAGPHSPTAQIIVELKNGRKLSLD     (SEQ ID NO:1) |
| βpep-8 |
| ANIKLSVEMKLFKRHLKWKIIVKLNDGRELSLD     (SEQ ID NO:2) |

TABLE 1-continued

Amino Acid Sequence of β-Peptides

βpep-11
ANIKLSVEMKLFCY$^D$WKVCKHVKLNDGRELSLD (SEQ ID NO:3)

βpep-1
SIQDLNVSMKLFRKQAKWKIIVKLNDGRELSLD (SEQ ID NO:4)

βpep-2
ANIKLSVKWKAQKRFLKMSINVDLSDGRELSLD (SEQ ID NO:5)

βpep-3
HIKELQVKWKAQKRFLKMSIIVKLNDGRELSLD (SEQ ID NO:6)

βpep-4
SIQDLNVSMKLFRKQAKWKINVKLNDGRELSLD (SEQ ID NO:7)

βpep-6
HIKELQVRWRAQKRFLRMSIIVKLNDGRELSLD (SEQ ID NO:8)

βpep-7
HIKELQVKMKAQKRFLKWSIIVKLNDGRELSLD (SEQ ID NO:9)

βpep-9
ANIKLSVKWKAQKRFLKMSIIVKLNDGRELSLD (SEQ ID NO:10)

βpep-10
ANIKLSVEMKLFCRHLKCKIIVKLNDGRELSLD (SEQ ID NO:11)

βpep-12
ANIKLSVEMKFFKRHLKWKIIVKLNDGRELSLD (SEQ ID NO:12)

βpep-13
ANIKLSVEFKLFKRHLKWKIIFKLNDGREFSLD (SEQ ID NO:13)

βpep-14
SIQDLNVSMKLFRKQAKWKLIVKLNDGRELSLD (SEQ ID NO:14)

βpep-15
SIQDLNVSMKLFRKQAKWKIILKLNDGRELSLD (SEQ ID NO:15)

βpep-16
SIQDLNVSMKLFRKQAKWKIIAKLNDGRELSLD (SEQ ID NO:16)

βpep-17
SIQDLNVSMKLFRKQAKWKILVKLNDGRELSLD (SEQ ID NO:17)

βpep-18
SIQDLKVSMKLFRKQAKWKIIVKLNDGRELSLD (SEQ ID NO:18)

βpep-19
SIQKLNVSMKLFRKQAKWKIIVKLNDGRELSLD (SEQ ID NO:19)

βpep-20
SIQDLNVSMXLFRKQAKWKIIVKLNDGRELSLD (SEQ ID NO:20)
"X" in this sequence refers to the noncommon aminoacid norleucine βpep-21
SIQDLNVSLKLFRKQAKWKIIVKLNDGRELSLD (SEQ ID NO:21)

βpep-22
SIQDLNLSMKLFRKQAKWKIIVKLNDGRELSLD (SEQ ID NO:22)

βpep-23
SIQDLKVSLNLFRKQAKWKIIVKLNDGRELSLD (SEQ ID NO:23)

βpep-24
SIQFLKVSLNLDRKQAKWKIIVKLNDGRELSLD (SEQ ID NO:24)

βpep-25
ANIKLSVQMKLFKRHLKWKIIVKLNDGRELSLD (SEQ ID NO:25)

βpep-26
SIQDLNVSMKLFRKQAKWKIIIKLNDGRELSLD (SEQ ID NO:26)

βpep-27
SIQDLNVSMKLFRKQAKWKAIVKLNDGRELSLD (SEQ ID NO:27)

βpep-28
SIQDLNVSMKLFRKQAKWKVIVKLNDGRELSLD (SEQ ID NO:28)

βpep-29
SIQDLNVSMKLFRKQAKWKLILKLNDGRELSLD (SEQ ID NO:29)

βpep-30
SIQDLNVSMKLFRKQAKWKVIIKLNDGRELSLD (SEQ ID NO:30)

Synthesized peptides used portions of human PF4 residues 22 to 54, IL-8 residues 22 to 54, and Gro-α residues 24 to 56. The C-terminal aspartic acid residue Cα carboxylate was made in the amide form. To avoid potential problems with cysteine oxidation, cysteines found in native sequences were replaced by serines. The native sequences for the PF4 (Deuel et al., *Proc. Natl. Acad. Sci USA* 74:2256–2258, 1977), IL-8 (Holt, et al. *Sem. Hematol.* 22:151–163, 1985) and GRO (Anisowicz et al., Proc. Natl. Acad. Sci. USA 84:7199–7192, 1987) peptide fragments are provided in FIG. 1.

βpep-5 was composed primarily of sequences from the α-chemokines platelet factor 4 (PF4) and interleukin-8 (IL-8). Turn/loop 1 and 2 are from PF4. Turn 2 is the PF4 peptide folding initiation site. The three strands were mostly from IL-8 with a few variations. The N-terminal dipeptide VT was included to create a potential strand 1-2 hydrophobic V25-L45 pair; a threonine was placed at position 26 to increase β-sheet propensity and to maintain solubility. IL-8 peptide K44 and E50 positions were switched to be more like PF4 with K50 and to maintain any folding stability from a potential salt-bridge pair.

βpep-8, βpep-11 and βpep-1 used a combination of α-chemokine sequences (primarily from strands 2 and 3 with the loop/turn initiation sequence and alternative sequences in the first turn/loop and strand 1 which were derived in part from another polypeptide from this lab. Similar β-sheet alignments found in α-chemokine polypeptides PF4, IL-8 and growth related polypeptide (Gro-α) also were generally conserved in all four peptides. βpep-8 has the IL-8 sequence I41-D54 (IIVKLSDGRELSLD) with the remainder of the sequence derived from the β-sheet domain of bactericidal/permeability increasing polypeptide. Three N-terminal residues 24, 26 and 28 from strand 1 were replaced with I,L,V for proper hydrophobic pairings with strand 2 residues. The number of residues in turn 1 was increased by one, thereby shifting the N-terminal numbering for paired residues by one relative to the α-chemokines.

βpep-11 differed from βpep-8 only in the first turn/loop, residues 34–39. In βpep-11, a tight turn motif containing a D-tryptophan, i.e., Y$^D$WKV, from somatostatin was used. Although two cysteines (for future oxidation to cysteine) were also present in βpep-11 as in somatostatin, they were maintained in the reduced state ($10^{-4}$ M perdeuterated mercaptoethanol was added to the solution). βpep-1 was based on βpep-8 with residues L26, V28, M30-F33 and K38-D54 being the same. The βpep-1 N-terminus (S22–S29) was taken from another α-chemokine polypeptide, neutrophil activating peptide-2 (NAP-2), and turn/loop residues 34–37 were conservative substitution from those in βpep-8.

TABLE 2

Amino acid compositions of β-sheet-forming peptides.

|  | βpep5 (3582)[1] | βpep8 (3969)[1] | βpep11 (3839)[1] | βpep1 (3859)[1] |
|---|---|---|---|---|
| HYDROPHOBIC | | | | |
| Ile | 4 | 3 | 3 | 3 |
| Leu | 4 | 6 | 5 | 5 |
| Val | 3 | 2 | 3 | 2 |
| Ala | 2 | 1 | 1 | 1 |
| Met | — | 1 | 1 | 1 |
| Phe | 1 | 1 | 1 | 1 |
| Tyr | — | — | 1 | — |
| Trp | — | 1 | 1 | 1 |
| Pro | 2 | — | — | — |
| TOTAL HYDROPHOBIC | 16 | 15 | 16 | 14 |
| Gly | 2 | 1 | 1 | 1 |
| CHARGED | | | | |
| Asp(−) | 1 | 2 | 2 | 3 |
| Glu(−) | 1 | 2 | 2 | 1 |
| Lys(+) | 4 | 6 | 5 | 5 |
| Arg(+) | 2 | 2 | 1 | 2 |
| His(+) | 1 | 1 | — | — |
| NONCHARGED POLAR | | | | |
| Asn | 1 | 2 | 2 | 2 |
| Gln | 1 | — | — | 2 |
| Thr | 2 | — | — | — |
| Ser | 2 | 2 | 2 | 3 |
| Cys | — | — | 2 | — |
| TOTAL POLAR (charged plus noncharged) | 15 | 17 | 16 | 18 |

[1]calculated molecular weight of peptide.

EXAMPLE 2

Circular Dichroism (CD) of the β-Peptide Series

Circular dichroism (CD) is one way to measure formation of a β-sheet structure. CD spectra were measured on a JASCO JA-710 (Jasco, Eastern, Md.) automatic recording spectropolarimeter coupled with a data processor. Curves were recorded digitally and fed through the data processor for signal averaging and baseline subtraction. Spectra were recorded from 5° C. to 65° C. in the presence of 10 mM potassium phosphate, over a 185 nm to 250 nm range using a 0.5 mm path-length, thermally-jacketed quartz cuvette. Temperature was controlled by using a NesLab water bath. Peptide concentration was varied from 0.014 to 0.14 mM. The scan speed was 20 nm/min. Spectra were signal-averaged 8 times, and an equally signal-averaged solvent baseline was subtracted. These experiments are well known in the art.

For βpep-5, CD data resembled those observed for β-sheet-forming PF4 peptide. Based on CD data alone, βpep-5 appeared not to form any β-sheets. CD data for all β peptides except βpep-5 showed a prominent band at 217 nm indicating formation of β-sheet structure. These peptides were composed mostly of β-sheet structure. For βpep-1, it was surprising that the normally "random coil" 204–208 nm CD band was also prominent given NMR results, which indicated that βpep-1 formed one of the most stable and compact β-sheet structure of all 30 peptides. It may be that this band, which shifts from 204 nm to 208 nm as the 217 nm β-sheet band becomes more negative, was the result of stable turn structure.

To demonstrate that temperature modulated β-sheet folding in these βpep peptides, the molar ellipticity at 217 nm for βpep-8, βpep-11 and βpep-1 was plotted versus temperature as seen in FIG. 2. As the temperature increased from 5° C., the 217 nm band became more negative (especially for βpep-11 and βpep-1) and leveled off between 35° C. and 50° C., indicating an increase in the β-sheet population. This "cold melt" demonstrated a role for the hydrophobic effect in stabilizing β-sheet conformational populations. For βpep-8, in particular, the 217 nm band became much more positive as the temperature increased further. This effect reflected a more traditional structural "melt." For βpep-11 and βpep-1, however, temperature increases up to 65° C. showed less of an effect on the β-sheet population. These data suggested that β-sheets in βpep-11 and βpep-1 are relatively more "stable" than in βpep-8. βpep-14 through βpep-30 also formed relatively stable compact β-sheets.

Those of ordinary skill in the art will readily recognize that the analyses performed for βpep-5, βpep-8, βpep-11 and βpep-1 can readily be performed for all 30 of the βpep peptides of this invention as well as any number of peptides prepared using the methods of this invention.

EXAMPLE 3

Nuclear Magnetic Resonance (NMR) of the β-Peptide Series

Figure 3:
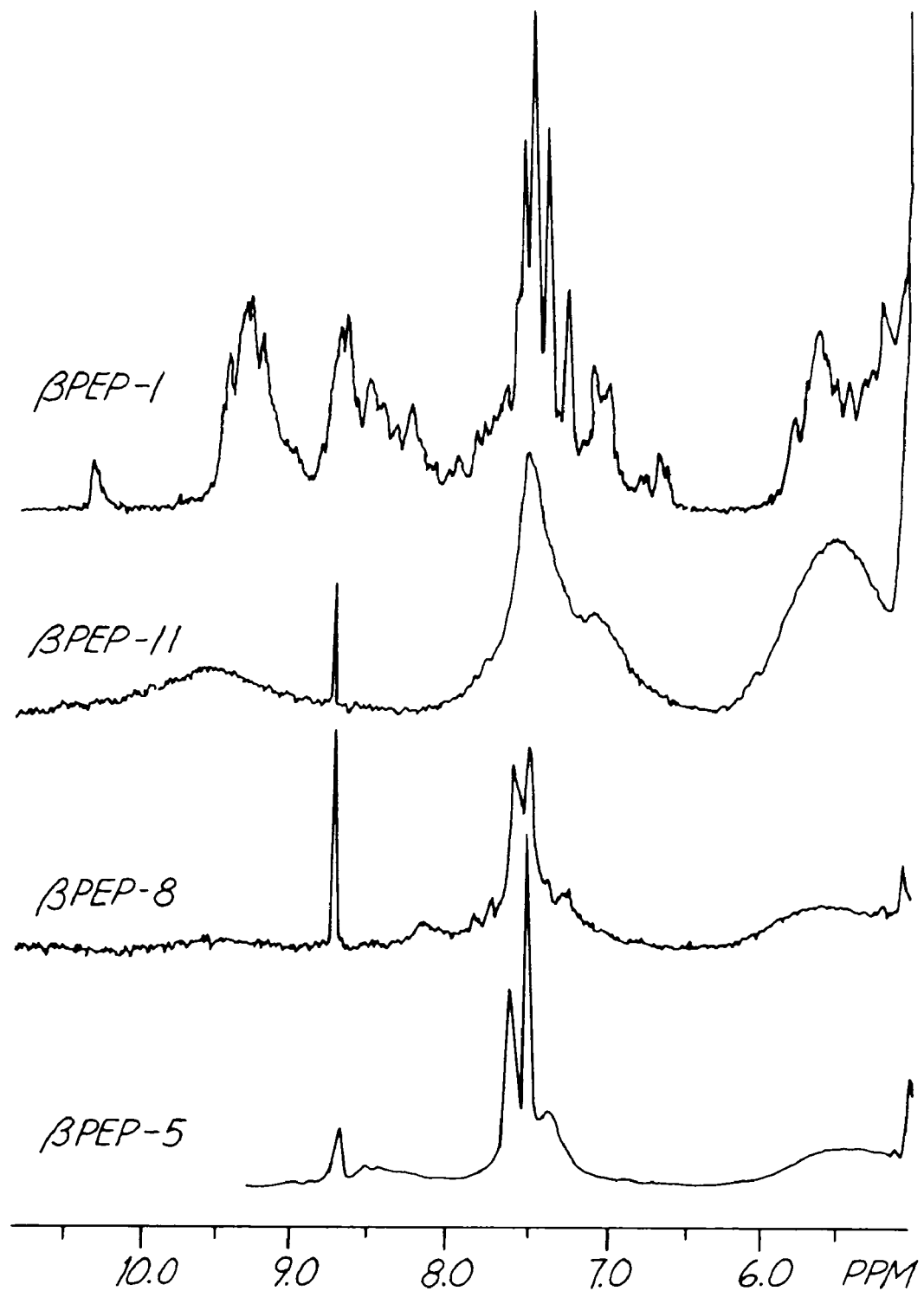
FIG. 3 is a graph depicting the $^1$HNMR spectra for βpep-5, βpep-8, βpep-11 and βpep-1 in H$_2$O at 600 MHZ. Peptide concentration was 20 mg/ml in 20 mM potassium phosphate at a temperature of 40° C. and a pH of 6.3. Spectra were accumulated with 8,000 data points over 6000 Hz sweep width and were processed with 3 Hz line broadening. Only the spectral region downfield from the HDO resonance is shown.

Since CD data indicate maximal β-sheet formation at about 40° C., NMR spectra (FIG. 3) were accumulated for βpep-5, βpep-8, βpep-11 and βpep-1 and the other peptides at pH 6.3, 20 mM NaCl and 40° C. For NMR measurements, freeze-dried peptide was dissolved either in $D_2O$ or in $H_2O/D_2O$ (9:1). Polypeptide concentration normally was in the range of 1 to 5 mM. pH was adjusted by adding μL quantities of NaOD or DCl to the peptide sample. NMR spectra were acquired on a Bruker AMX-600 (Bruker Instrument, Inc., Bruker, Mass.) or AMX-500 NMR spectrometer. For resonance assignments, double quantum filtered COSY (Piantini et al. *J. Am. Chem. Soc.* 104:6800–6801, 1982) and 2D-homonuclear magnetization transfer (HOHAHA) spectra, obtained by spin-locking with a MLEV-17 sequence with a mixing time of 60 ms, were used to identify spin systems (See Bax, et al. *J. Magn. Reson.* 65: 355–360, 1985). NOESY experiments (see Jeener et al., *J. Chem. Phys.* 71:4546–4553, 1979 and Wider et al. *J. Magn. Reson.* 56:207–234, 1984) were performed to sequentially connect spin systems and to identify NOE connectivities. All 2D-NMR spectra were acquired in the TPPI (Marion & Wüthrich, *Biochem. Biophys. Res. Comun.* 113:967–974, 1983) or States-TPPI (States et al. *J. Magn. Reson.* 48:286–292, 1982) phase sensitive mode. The water resonance was suppressed by direct irradiation (0.8 s) at the water frequency during the relaxation delay between scans as well as during the mixing time in NOESY experiments. These experiments are well-known in the art.

2D-NMR spectra were collected as 256 to 400 t1 experiments, each with 1k or 2k complex data points over a spectral width of 6 kHz in both dimensions with the carrier placed on the water resonance. For HOHAHA (COSY) and NOESY spectra, normally 16 and 64 scans, respectively, were time averaged per t1 experiment. The data were processed directly on the Bruker AMX-600 X-32 or offline on a Bruker Aspect-1 workstation with the Bruker UXNMR program. Data sets were multiplied in both dimensions by a 30–60 degree shifted sine-bell function and zero-filled to 1k in the t1 dimension prior to Fourier transformation.

NMR data indicated that βpep-1 was best of βpep-5, βpep-8, βpep-11 and βpep-1 at forming a compact, triple-stranded β-sheet peptide tetramer by virtue of the presence of relatively well-defined, downfield shifted αH and NH resonances. Assuming a similar β-sheet alignment and number (13 to 16) of downfield shifted αH resonances as found in any native α-chemokine and normalizing to the aromatic resonance area (10 protons), it was estimated that this αH resonance area represents a fully folded βpep-1. Compared to betabellin 14D, NMR resonances of the β-sheet folded state for betabellin 14D were broader than would be expected for a dimer of its size, indicating formation of larger aggregates. Moreover, betabellin 14D folding was also apparently not as compact as that found in βpep-1.

NMR spectra for βpep-5, βpep-8 and βpep-11 also showed downfield shifted αH and NH resonances, which indicates β-sheet formation. While CD data suggested greater than 90% β-sheet structure for βpep-8 and βpep-11, NMR data suggested somewhat less. CD data, however, would give evidence for significant β-sheet structure even if it were highly transient in a molten globule-like or non-compact state. The presence of these downfield shifted NMR αH resonances, therefore, indicated populations of relatively well-formed β-sheet conformation which are in slow chemical exchange (600 MHZ NMR chemical shift time scale) with "non-compact" or "unfolded" conformational states whose αH protons resonate more upfield. For βpep-11, downfield shifted NHs were present in $D_2O$ for an extended period of time (4 hours), supporting the idea of some structural stability. Downfield shifted αH and NH resonances, however, were very broad with an overall envelope half-height of about 500 Hz. Although this resonance broadening could be the result of this exchange process, the possibility of intermediate exchange among similarly folded β-sheet conformations or exchange among aggregate states were also investigated.

EXAMPLE 4

Pulsed-Field Gradient (PFG) NMR Self-Diffusion Measurements of β-Peptide Series Peptides Pulsed-field gradient (PFG) NMR diffusion measurements (Gibbs, et al. *J. Magn. Reson* 93:395–402, 1991) were performed on βpep peptides to assess self-association properties. Pulsed field gradient (PFG) NMR self-diffusion measurements were made on a Bruker AMX-600 using a GRASP gradient unit. NMR spectra for measurement of diffusion coefficients, D, were acquired using a 5 mm triple-resonance probe equipped with an actively shielded z-gradient coil. The maximum magnitude of the gradient was calibrated by using the standard manufacturer's (Bruker) procedure and was found to be 60 G/cm which is consistent with the value of 61 G/cm obtained from analysis of PFG data on water using its known diffusion constant. The PFG longitudinal eddy-current delay pulse-sequence was used for all self-diffusion measurements which were performed in $D_2O$ over the temperature range 275° K to 310° K Peptide concentrations ranged from 3 mg/mL to 10 mg/mL.

For unrestricted diffusion of a molecule in an isotropic liquid, the PFG NMR signal amplitude normalized to the signal obtained in the absence of gradient pulses is related to D by:

$$R = \exp[-\gamma^2 g^2 \delta^2 D(\Delta - \delta/3)]$$

where γ is the gyromagnetic ratio of the observed nucleus; g and δ are the magnitude and duration of the magnetic field-gradient pulses, respectively, and Δ is the time between the gradient pulses. For these studies, experimental conditions were: δ=4 ms, g=1 to 45 G/cm, Δ=34.2 ms, and the longitudinal eddy-current delay $T_e$=100 ms. Each diffusion constant was determined from a series of 15 one dimensional PFG spectra acquired using different g values. Experimental decay curves were approximated as single exponentials.

Diffusion coefficients for peptides were calibrated by performing the same PFG NMR self-diffusion measurements on globular polypeptides lysozyme, ribonuclease and ubiquitin. Here, PFG measurements yielded D values at 20° C. of $10.1 \times 10^{-7}$ $cm^2/s$ for lysozyme, $10.2 \times 10^{-7}$ $cm^2/s$ for ribonuclease, and $14.3 \times 10^{-7}$ $cm^2/s$ for ubiquitin. These D values were within those values in the literature: $10.6 \times 10^{-7}$ $cm^2/s$ for lysozyme obtained from light scattering by extrapolation to infinite dilution; $10.7 \times 10^{-7}$ $cm^2/s$ for ribonuclease also obtained from light scattering by extrapolation to infinite dilution, and $14.9 \times 10^{-7}$ $cm^2/s$ for ubiquitin (Altieri et al., *J. Am. Chem. Soc.* 117: 7566–7567, 1995) obtained by using similar PFG NMR measurements. This relatively good agreement in diffusion coefficients indicated that the PFG longitudinal eddy-current delay pulse sequence allows derivation of accurate diffusion constant values.

The Stokes-Einstein relationship $D = k_B T / 6\pi \eta R$ was used to relate D to the macro-molecular radius, R, which was considered to be proportional to the square root of the apparent molecular weight, $M_{app}^{1/2}$ (Cantor et al. 1980. *The behavior of biological macromolecules*. Biophysical Chemistry, part III. New York: W. H. Freeman. pp. 979–1039). Therefore, D is proportional to $M_{app}^{-1/2}$. From these simple relationships, the ratio $D_{dimer}/D_{monomer}$ was 0.71, which is very close to 0.72 theoretically predicted for a two sphere dimer (Wills, et al. *J. Phys. Chem.* 85: 3978–3984, 1981). Use of the Stokes-Einstein relationship is specifically derived for a hard sphere, and although the actual molecular shape of each peptide aggregate would affect the diffusion coefficient, the maximum change in the ratio $D_{aggregate}/D_{monomer}$ would be about 20% in case of an improbable linear peptide tetramer. $M_{app}$ for peptides was calculated using D values of lysozyme, ribonuclease and ubiquitin as standards for monomers of known molecular weight.

Figure 4:
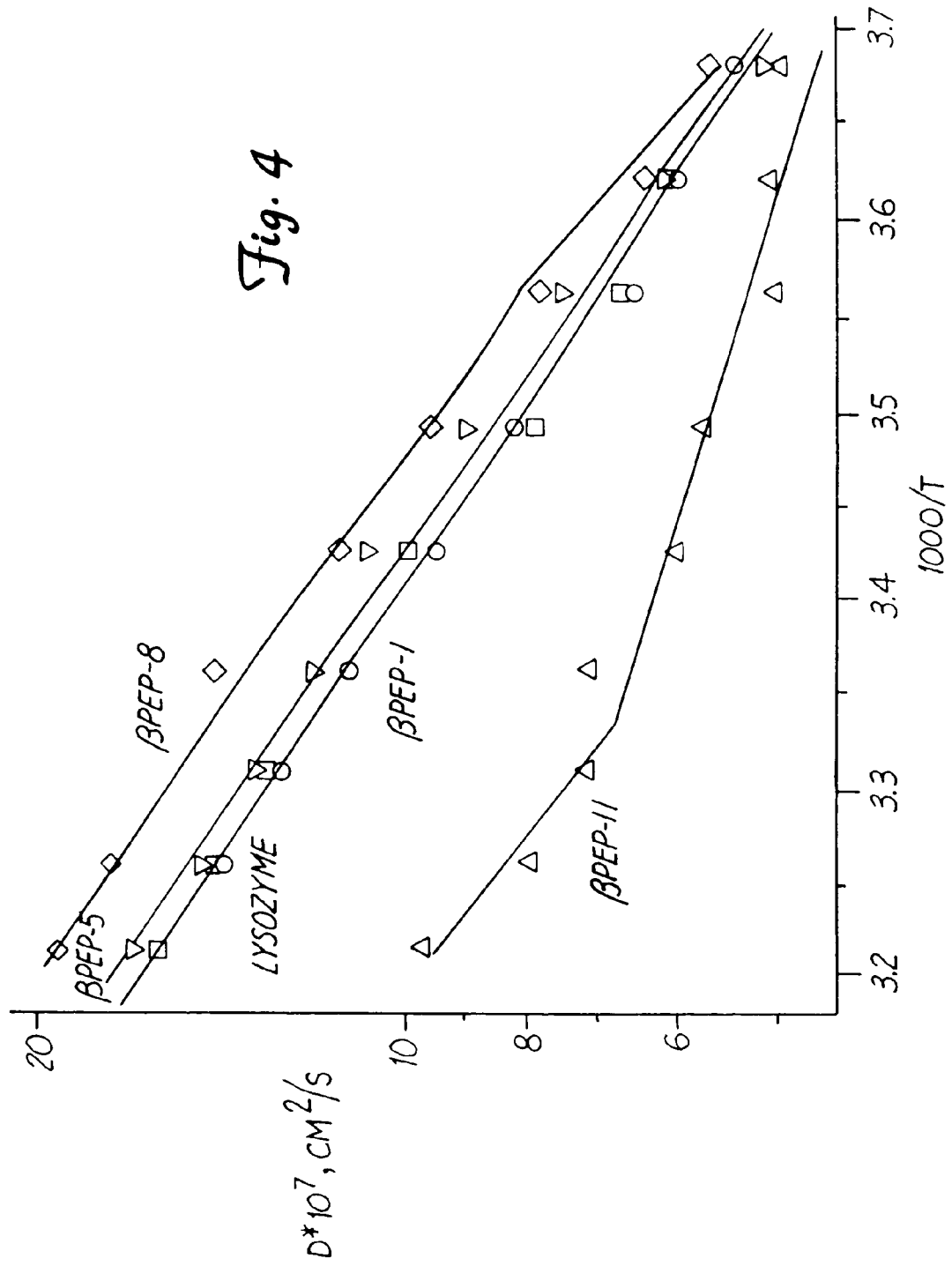
FIG. 4 is a graph showing pulsed-field gradient (PFG) NMR diffusion coefficients as a function of temperature for βpep-5, βpep-8, βpep-11, βpep-1 and lysozyme.

The temperature dependence of diffusion coefficients is plotted in FIG. 4. By calibrating with diffusion data on lysozyme, ubiquitin, and ribonuclease, the average molecular weight for these peptides at 30° C. was determined: βpep-5=12,750; βpep-8=9,490; βpep-11=41,200, and βpep-1=13,700. Moreover, for βpep-5, βpep-8 and βpep-1, the temperature dependence was linear and followed the activation energy expected for the self-diffusion of water. However, the aggregate state distribution changed for βpep-8 below 10° C. and for βpep-11 over any temperature range investigated. For βpep-5 and βpep-1, the average molecular weight derived from these diffusion constants divided by the calculated monomer molecular weight (Table 1) yielded a ratio of 3.6. Since the temperature dependence of the diffusion constants was linear, the aggregate state distribution is unchanged, suggesting that a single aggregate state was present. βpep-1 showed compact β-sheet structure; βpep-5 was less clear. Given the fact that these apparent molecular weights were not being corrected for shape and electrostatic effects, the derived aggregate molecular weights can be subject to some variation. Therefore, βpep-1 may fold as a compact tetramer, and while βpep-5 also may tetrameric, there may be some distribution of monomer-dimer-tetramer. In general, these peptides formed tetramers.

A distribution of aggregate states was present in βpep-8 and βpep-11. The βpep-8 slope remained linear between 10° C. and 40° C. and deviated from linearity at lower temperatures. The ratio of its apparent molecular weight to its calculated monomer molecular weight (see Table 1) was 2.4 up to 10° C. and changed to 3.7 by 2° C. These data suggested that βpep-8 is on average a dimer and increased its aggregation state, probably to a tetramer, at lower temperatures. βpep-11 showed most unusual diffusion characteristics. Its aggregate state distribution continually changed with temperature. At lower temperature, its average molecular weight was that of a tetramer, while at higher temperatures, large aggregates upwards of octamers appeared to form.

EXAMPLE 5

Endotoxin Neutralizing Activity and Bactericidal Activity of βpep-5, βpep-8, βpep-11 and βpep-1

The peptides were tested for their ability to neutralize endotoxin. Quantitative endotoxin activities for these peptides were measured by Limulus amoebocyte lysate assay.

Bacteria: *P. aeruginosa* type 1 is a clinical isolate maintained in the laboratory. The isolate remains a smooth strain and was serotyped by the scheme of Homma. The Pseudomonas strain was maintained by monthly transfer on blood agar plates.

Purification of B/PI: B/PI was purified in three column-chromatography steps. In the final step, the sample was applied to a 1×180 cm molecular sieving column of Toyopearl HW55S (TosoHaas, Philadelphia Pa.) which had been equilibrated with 0.05 M glycine buffer (pH 2.5) containing 0.5M NaCl. Polypeptide concentration was determined according to Hartree (*Analytical Biochem.* 48:422–427 (1972)). Purity was confirmed by visualization of a SDS polyacrylamide gel following electrophoresis of 1 μg of purified BP55 polypeptide and silver staining of the gel using techniques well known in the art.

*Limulus* amoebocyte lysate assay: The ability of synthetic peptides to neutralize endotoxin was detected with the E-TOXATE kit manufactured by Sigma Chemicals (St. Louis, Mo.). The concentration of peptide required to completely inhibit the coagulation of *Limulus* amoebocyte lysate driven by 0.04 unit (or 0.01 ng) of *E. coli* 055:B5 LPS was determined by dose response and as outlined in technical bulletin No. 210 of Sigma Chemicals. Peptide or B/PI was incubated with LPS at room temperature for 5 min in 100 ul of a 1:2 dilution of pyrogen-free saline (pH 6.4). The reaction was started by addition of 100 ul of amoebocyte lysate and the final volume was 200 ul. Assuming a 10,000 molecular weight for LPS, the approximate molar ration of B/PI:LPS at neutralization was 3000 to 1.

The peptides were tested according to the method provided above. PF4 (see FIG. 1) was used as a negative control and demonstrated no endotoxin neutralizing activity. BG38L corresponds to amino acids 86–108 of B/PI and domains within B/PI have been shown to demonstrate endotoxin neutralizing activity. BG38L was used as a positive control in these experiments. The endotoxin neutralizing data is provided below:

TABLE 3

Endotoxin Neutralizing Activity

| Peptide | Endotoxin Neutralizing[a] Activity $5.0 \times 10^{-5}$ M peptide |
|---|---|
| βpep-5 | 70.3, n = 3 |
| βpep-8 | 100 ED[c] $1.2 \times 10^{-6}$ M, n = 7 |
| βpep-11 | 100 ED[c] $1.2 \times 10^{-6}$ (29.5), n = 5 |
| βpep-1 | 42.8, n = 3 |
| PF4 | 0 ED[c] $5.0 \times 10^{-5}$ (23), n = 1 |
| BG38 | 34.4, n = 5 |

[a]% neutralization of 0.02 U(0.2 pg of endotoxin from *E. coli* 055:B5)
[b]% killing of $5 \times 10^5$ *P. aeruginosa*
[c]Effective M dose (%)

This data demonstrates that the β peptides of this invention were effective at neutralizing endotoxin activity.

EXAMPLE 6

Assay to Determine Bactericidal Activity

The peptides can be assayed for bactericidal activity against a variety of organisms such as *Pseudomonas aeruginosa* type 1, *P. cepacia* ATCC 25608, *E. coli* B, and *Staphylococcus aureus* 502A by standard methods.

*Pseudomonas aeruginosa* type 1 is a clinical isolate. The isolate remains a smooth strain and was serotyped by the scheme of Homma (*Jpn. J. Exp. Med.* 46:329, 1976). A rough strain, *E. coli* B and *S. aureus* 502A were obtained from Paul Quie, University of Minnesota (Minneapolis, Minn.). The characteristics of the *S. aureus* strain have been described by Shinefield et al. (*Amer. J. Dis. Chil.* 105:646, 1963). *Pseudomonas cepacia* ATCC 25608 can be purchased from the ATCC. *S. aureus* and *E. coli* were maintained on nutrient agar plates and the *Pseudomonas* strains were maintained on blood agar plates.

Pyrogen-free solutions were used throughout the assay and all methods that follow. Log phase bacteria were prepared from a culture in brain heart infusion broth (Hovde et al. *Infect. Immun.* 54:142–148, 1986) and bacteria were washed and resuspended in saline with adjustment to an optical density at 650 nm to provide a yield of about $3 \times 10^8$ CFU/ml. Bacteria were diluted 1:10 in 0.08M citrate phosphate buffer, pH 5.6 or pH 7.0, for use in the assay. *S. aureus* rapidly lost viability in the pH 5.6 buffer and was studied only at pH 7.0. Bactericidal activity was determined by dose response over peptide concentrations ranging from about $1.2 \times 10^{-1}$M to about $4.1 \times 10^{-9}$M. Bactericidal activity was determined by dose response, preferably determining LD$_{50}$ by linear regression.

Results are as follows:

TABLE 4

Endotoxin Neutralizing Activity and Bactericidal Activity of βpeptides

| Peptide | Endotoxin Neutralization.[a] $5.0 \times 10^{-6}$ M Peptide | Bactericidal Activity[b] $1.2 \times 10^{-7}$ M Peptide |
|---|---|---|
| βpep-1 | 42.8, n = 3 | 32.0, n = 3 |
| βpep-2 | 55.3, n = 5 | 18.8, n = 6 |
| βpep-3 | 79.4, n = 10 | 24.9, n = 3 |

TABLE 4-continued

Endotoxin Neutralizing Activity and Bactericidal Activity of βpeptides

| Peptide | Endotoxin Neutralization.[a] $5.0 \times 10^{-6}$ M Peptide | Bactericidal Activity[b] $1.2 \times 10^{-7}$ M Peptide |
|---|---|---|
| βpep-4 | 14.7, n = 3 | 37.6, n = 3 |
| βpep-5 | 70.3, n = 3 | 7.4, n = 7 |
| βpep-6 | 79.3, n = 3 | 8.2, n = 2 |
| βpep-7 | 77.7, n = 2 | 39.1, n = 2 |
| βpep-8 | 100 Ed[c] $1.2 \times 10^{-6}$(77.9) n = 7 | 0 Ed[c] $9.6 \times 10^{-7}$ (28.1), n = 3 |
| βpep-9 | 100 Ed[c] $1.2 \times 10^{-6}$(32.3) n = 9 | 0 Ed[c] $9.6 \times 10^{-7}$ (47.4), n = 11 |
| βpep-10 | 100 Ed[c] $1.2 \times 10^{-6}$(25.2) n = 8 | 0 Ed[c] $9.6 \times 10^{-7}$ (20.9), n = 7 |
| βpep-11 | 100 Ed[c] $1.2 \times 10^{-6}$(29.5) n = 5 | 0 Ed[c] $9.6 \times 10^{-7}$ (48.0), n = 4 |
| βpep-12 | 100 Ed[c] $1.2 \times 10^{-6}$(29.5) n = 3 | 0 Ed[c] $9.6 \times 10^{-7}$ (49.1), n = 5 |
| βpep-13 | 100 Ed[c] $1.2 \times 10^{-6}$(22.5) n = 1 | 0 Ed[c] $9.6 \times 10^{-7}$ (19.8), n = 3 |
| βpep-14 | 38.8 n = 1 | 0 Ed[c] $9.6 \times 10^{-7}$(39.9), n = 3 |
| βpep-15 | 48.1 n = 1 | 0 Ed[c] $9.6 \times 10^{-7}$(23.9), n = 3 |
| βpep-16 | 100 Ed[c] $1.2 \times 10^{-6}$(16.5) n = 3 | 0 Ed[c] $9.6 \times 10^{-7}$(24.3), n = 3 |
| βpep-17 | 100 Ed[c] $1.2 \times 10^{-6}$(28.9) n = 3 | 0 Ed[c] $9.6 \times 10^{-7}$(40.1), n = 4 |
| βpep-18 | 100 Ed[c] $1.2 \times 10^{-6}$(30.2), n = 1 | 18.8, n = 1 |
| βpep-19 | 0 Ed[c] $1.6 \times 10^{-5}$(12.4), n = 2 | 62.5, n = 2 |
| βpep-20 | 100 Ed[c] $1.2 \times 10^{-6}$(17.1), n = 1 | 0 Ed[c] $4.8 \times 10^{-7}$(0.0), n = 4 |
| βpep-21 | 100 Ed[c] $1.2 \times 10^{-6}$(40.3), n = 1 | 13.0, n = 1 |
| βpep-22 | 100 Ed[c] $1.2 \times 10^{-6}$(21.3), n = 4 | 35.5, n = 3 |
| βpep-23 | 100 Ed[c] $1.2 \times 10^{-6}$(65.7), n = 3 | 0 Ed[c] $4.8 \times 10^{-7}$(45.8), n = 3 |
| PF4 | 0 Ed[c] $5.0 \times 10^{-5}$(0), n = 2 | 0 Ed[c] $1.5 \times 10^{-6}$(19), n = 2 |

[a]% neutralization of 0.02 U(0.2 pg of endotoxin from E. coli 055:B5
[b]% killing of $5 \times 10^5$ P. aeruginosa
[c]Effective M dose (%)

The best endotoxin neutralizing activity was identified for βpep-8 and βpep-23. The peptides tested that had the greatest bactericidal activity included βpep-19, βpep-7, βpep-4, βpep-22 and βpep-1.

EXAMPLE 7

βpep-3 as an Endotoxin Agonist

All peptides, BG22 (a 27mer, BPI aa 82–108), βpep-3 (SEQ ID NO:6) and BG16 (control peptide derived from a portion of BPI exclusive of the LPs binding domain, aa 170–199), were synthesized at the University of Minnesota microchemical facility using a mMillgren bioresearch 9600 peptide synthesizer as described (Mayo et al. *Protein Science* 5:1301–1315, 1996). Amino acid composition of the peptides was confirmed by gas-phase Edman degradation, using an Applied Biosystems 470A gas-phase sequenator with a reverse-phase C18 column. Purified peptides were resuspended in pyrogen-free PBS prior to their use in all experiments. The structure of βpep-3 was confirmed by two dimensional nuclear magnetic resonance and circular dichroism spectroscopy as described by Ilyine E. et al. (*Biochem J.* 306:407–419, 1995).

Underlined amino acid sequence represents the LPS binding domain of BPI
italicized sequences are derived from the amino acid residues responsible for initiation of β-turning in native IL-8.

LPS derived from *P. aeruginosa* and *E. coli* 0111:B4 or 055:B5 was purchased from List Biological Laboratories (Campbell, Calif.) and stored at 4° C. until use. A commercially available chromogenic *Limulus* amoebocyte lysate test (Whittaker, Walkersville, Md.) was used to measure endotoxin levels in all solutions and serum samples. Endotoxin levels in peptide solutions were determined to be less than about 0.1 ng/ml. The capacity of BG22, βpep-3 and BG16 to neutralize *E. coli* 055:B5 endotoxin in vitro was determined by mixing 0.01 ng of LPS with $5 \times 10^{-6}$M of each peptide and results were compared to that observed for 0.01 ng of LPS alone.

$5 \times 10^{-5}$ RAW 264.7 cells were placed in each well of a 24-well culture plate and allowed to adhere. Immediately before LPS stimulation, medium was removed and cells were washed in serum-free Dulbecco's modified Eagle's medium (DMDM). Cells were incubated at 37° C. in a 10% $CO_2$ atmosphere for 3 hours with: 1) DMEM alone, 2) *E. coli* 0111:B4 LPS alone, or 3) *E. coli* 0111:B4 LPS preincubated with BG22, βpep-3 or BG16. The concentration of LPS used in all groups was 200 ng/ml. To avoid non-specific inhibition of LPS-induced TNF-α secretion, $10^{-5}$ M of each peptide was used in the experimental wells. At the end of the incubation period, macrophage supernatants were collected and assayed for TNF-α concentration.

TNF-α concentrations were measured as described by Battafarano et al. (supra). Briefly, the TNF-α sensitive cell line WEHI was used in all assays of either RAW cell supernatant (in vitro) or serum (in vivo animal model). Concentrations were extrapolated from a standard curve based oil dilutions of purified TNF-α (Genzyme, Cambridge, Mass.), and all samples were examined in triplicate. Viability of the WEHI cells was assessed by measuring the extent of cellular crystal violet uptake by spectrophotometry at 590 nm. In this assay, absorbance was inversely correlated with cell death and lysis resulting from exposure of WEHI cells to TNF-α. The amount of TNF-α in each experimental sample was extrapolated from the standard curve.

To study endotoxemia in a mammal, 500 μg of each peptide was added to 8 μg of *Pseudomonas aeruginosa* LPS in 2.0 ml of pyrogen-free phosphate buffered saline (PBS) ex vivo, and incubated for 30 minutes on a shaker at room temperature. Each mouse was injected via tail vein with 0.5 ml of the mixture (125 μg of BG22, BG16, or βpep-3 and 2 μg of LPS per mouse). Mice were euthanized at 30, 60, 90 and 120 minutes after injection and serum collected just prior to death was analyzed for endotoxin levels and TNF-α concentration.

All TNF-α and endotoxin measurements in duplicate or triplicate in each experiment. In vivo experiments were performed twice to confirm reproducibility. The results obtained were compared using the unpaired Student's t-test.

Figure 5:
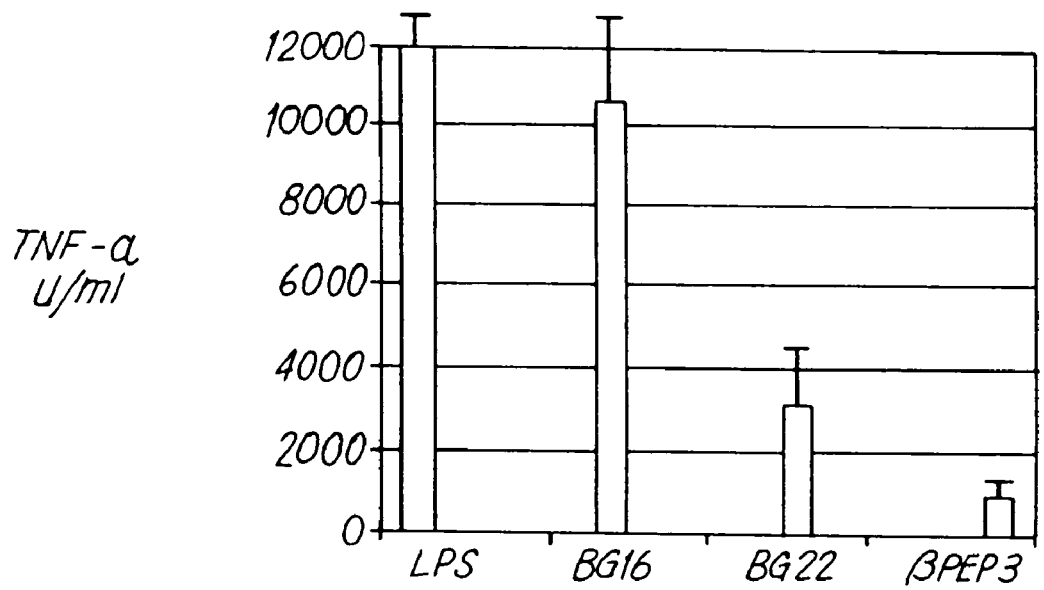
FIG. 5 is a graph demonstrating the capacity of anti-endotoxin peptides BG22 and βpep-3 to diminish LPS-induced secretion of TNF-α in vitro by RAW 264.7 cells.
Figure 6:
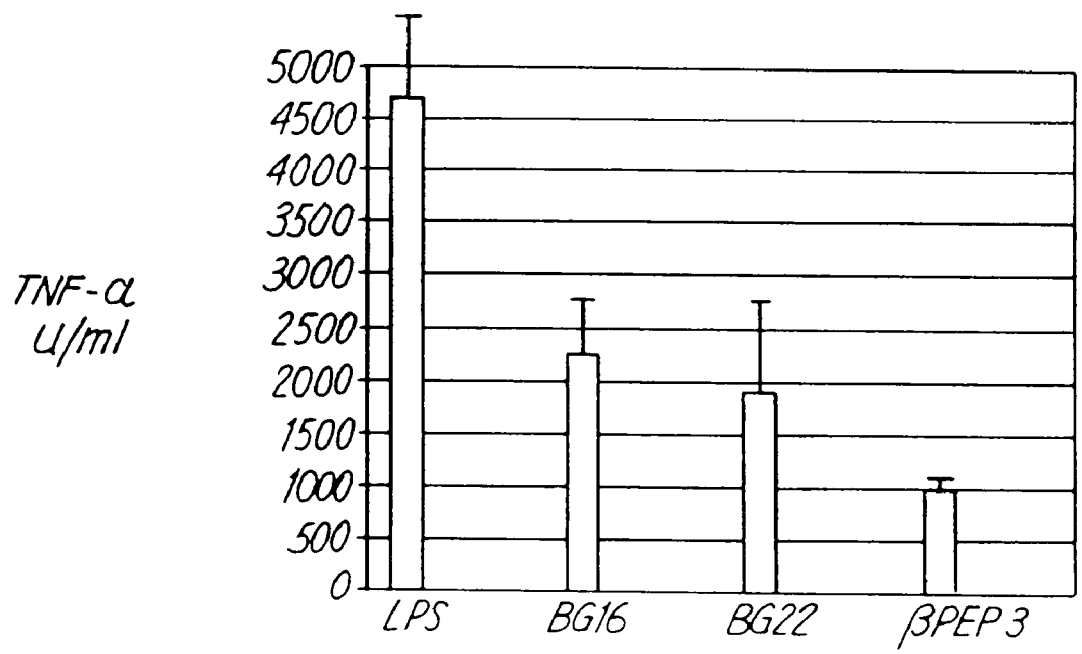
FIG. 6 is a graph demonstrating the capacity of anti-endotoxin peptides BG22 and βpep-3 to diminish TNF-α secretion during endotoxemia in vivo. Data are provided at 90 minutes post-challenge.

FIG. 5 provides the results of studies to determine the capacity of βpep-3 to diminish LPS-induced secretion of

| BG22 | 82-108BPI | NANIKISG*KWKAQKRFLKM*SGNFDLSI | (SEQ ID NO:31) |
| Bpep-3 | BPI/IL-8 | *HIKELQV*KWKAQKRFLKMS*IIVKLNDGRELSLD* | (SEQ ID NO:3) |
| BG16 | 170-199BPI | MNSQVCEKVTNSVSSKLQPYFQTLPVMTKI | (SEQ ID NO:32) |

TNF-α in vitro by RAW 264.7 cells. Both BG22 and βpep-3 neutralized endotoxin, compared to BG16 which lacked any endotoxin neutralizing capabilities (37% and 81% vs. 0%, respectively; p<0.05). Interestingly, βpep-3 neutralized LPS to a significantly greater degree than BG22 (see Table 5: p<0.05). Of note, preincubation with βpep-3 caused a significantly greater decrease in TNF-α secretion, compared to that which was observed for BG22 (p=0.04, FIG. 5).

Preincubation of LPS with peptides BG22 and βpep-3 prior to intravenous (IV) challenge led to a similar, significant dimunution in serum endotoxin levels at all time points measured (30, 60, 90, and 120 minutes), compared to BG16 or LPS without peptide (p<0.05,Table 6). Similarly, preincubation of either BG22 or βpep-3 with LPS before iv injection resulted in decreased serum TNF-α levels at 90 minutes post-challenge, compared to mice receiving LPS without peptide (p<0.05, FIG. 6). Either BG22 or βpep-3 injection resulted in decreased serum TNF-α levels compared to mice receiving LPS without peptide. Although there appeared to be greater inhibition of TNF-α in mice receiving the βpep-3 versus BG22, the difference was not statistically significant.

The endotoxin binding domain of PBI forms an amphipathic β-turn with alternativing charged and hydrophobic amino acid residues. This secondary structure can be important to effect binding interactions between the peptids and LPS. βpep-3 folds with a β-turn at physiologic pH.

Both βpep-3 and BG22 bound to endotoxin but βpep-3 was significantly more effective in neutralizing endotoxin in vitro, compared with BG22. In fact, this finding correlated with the ability of βpep to more effectively inhibit LPS induced TNF-α secretion by macrophages in vitro. Without intending to limit the scope of this invention, it seems likely that the factor that may account for the enhanced anti-endotoxin properties of βpep-3 in vitro is its folding such that it more closely resembles the LPS binding domains of the native anti-LPS proteins.

Both BG22 and βpep-3 demonstrated similar efficacy in vivo, as evidenced by a reduction in circulating endotoxin and diminished TNF-α secretion during murine endotoxemia. Several factors may account for the relative inability to notice a significant difference between these peptides in the murine model such as the competition for LPS binding by endogenous proteins (including, for example, LBP, lipopolysaccharide binding protein, and 2) rapid clearance or short half-life or small peptides. The binding affinity of βpep-3 can be enhanced via site-directed changes in amino acids and the biologic half-life of this peptide along with others prepared by the methods of this invention can be increased via conjugation of these peptides to larger, stable carrier proteins including, for example, keyhole limpet hemocyanin.

TABLE 5

Determination of the capacity of anti-endotoxin peptides BG22 and βpep-3 to neutralzine endotoxin in vitro. βpep-3 demonstrated enhanced capacity to neutralize endotoxin comapred to BG22 or BG16.

| Peptide | % Neutralization of Endotoxin |
|---------|-------------------------------|
| BG22    | 37%                           |
| βpep-3  | 81% (p < 0.05)                |
| BG16    | 0%                            |

TABLE 6

Determination of the capacity of anti-endotoxin peptides BG22 and βpep-3 to diminish endotoxemia in vivo. Both BG22 and βpep-3 significantly diminish endotoxemia compared to control peptide BG16.

| | Minutes after LPS/Peptide Injection | | | |
|---|---|---|---|---|
| | 30 | 60 | 90 | 120 |
| BG22 | 7* | 28* | 73* | 47* |
| βpep3 | 11* | 37* | 63* | 66* |
| BG16 | >10,000 | 2,394 | 5,599 | >10,000 |
| LPS | >10,000 | >10,000 | >10,000 | >10,000 |

*p < 0.05

EXAMPLE 8

βpeptide Series Peptides as Angiogenesis Inhibitors

To test the hypothesis that angiostatic factors can prevent or inhibit angiogenesis mediated downregulation of endothelial adhesion molecules, angiogenesis and endothelial cell proliferation, PF4, one of the most potent angiogenesis inhibitors, and its related βpep-peptides were tested for their effects on endothelial adhesion molecule expression from endothelial cells (EC). Like the native PF4, βpep-14 and βpep-16 peptides were found to be angiostatic as determined by measurement of EC proliferation in vitro (Table 7). We also studied the effect of the peptides on expression of intercellular adhesion molecule-1 (ICAM-1) since in earlier studies it was demonstrated, by the use of blocking antibodies, that ICAM-1/LFA-1 interaction was most important in leukocyte/EC adhesion and extravasation.

In a first series of experiments, PF4 and βpep peptides were tested for their ability to prevent bFGF (fibroblast growth factor) mediated downregulation of ICAM-1. It was found that inhibition of angiogenesis and endothelial cell proliferation resulted in a complete blockade of bFGF mediated ICAM-1 downregulation. A 3-day preincubation of EC with 10 ng/ml bFGF resulted in a marked modulation of ICAM-1. Simultaneously 100 µg/ml of each PF4, βpep-14, βpep-16, or medium was added. Mean ICAM-1 fluorescence intensity values were determined. The addition of 100 µg/ml PF4 enhanced the expression of ICAM-1. Simultaneous addition of bFGF and PF4 did not result in the loss of ICAM-1 expression. Also, the addition of the PF4 related peptides βpep-14 and βpep-16 resulted in a complete block of bFGF mediated downregulation.

Since the in vivo situation of tumor associated EC involves the low expression or even absence of ICAM-1, the next set of experiments aimed to study the ability to reinduce ICAM-I expression after bFBF preincubation. It had been demonstrated previously that the longevity of the bFGF mediated ICAM-1 downregulation is at least 7 days. Treatment of EC expressing downregulated ICAM-1 levels with 100 µg/ml PF4 resulted, even in the presence of bFGF, in reinduction of ICAM-1. βpep-14 and βpep-16 showed similar results. In these experiments, HUVEC were pretreated for 3 days with bFGF, subsequently PF4 was added for 3 days and, where indicated in the last 16 hours of culture 4 ng/ml TNFα was added. Human umbilical vein derived endothelial cells (HUVEC) were harvested from normal human umbilical cords by perfusion with 0.125% trypsin/EDTA as described previously. Cells were cultured in fibronectin (FN) coated tissue culture flasks in culture medium (RPMI-1640 with 20% human serum (HS), supplemented with 2 mM glutamine and 100 U/ml penicillin and 0.1 mg/ml streptomycin). Immunofluorescence using indirect PE-conjugated reagents required three separate incubations. 1×10⁵ EC were fixed for 1 hour in 1% paraformaldehyde, resuspended in 20 µl appropriately diluted Mab and incubated for 1 hour on ice. Subsequently, cells were washed two times in PBS/BSA (0.1%) and incubated for another 30 minutes with biotinylated rabbit-anti-mouse Ig (Dako, Glostrup, Denmark). After another 2 washings, cells were incubated with streptavidin-phycoerythrin conjugate (Dako). Stained cells were analyzed on a FACScan flowcytometer. Data analysis was performed using PCLysys software (Becton Dickinson, Mountain View, Calif.). Statistical significance of observed differences was determined using the Student's t-test.

The anergy of EC to stimulation with inflammatory cytokines was the subject of a next series of experiments. For these experiments, HUVEC (human vascular endothelial cells) were pretreated with 10 ng/ml bFGF for 3 days. Subsequently, cells are subcultured for 3 days with 100 µg/ml bFGF in the presence of PF4. For the last 16 hours of the culture 4 ng/ml TNFα was added to induce upregulation of ICAM-1. The decreased inflammatory response of angiogenic stimulated EC was found to be overcome by simultaneous treatment with PF4 and similar results were found for βpep-14 and βpep-16. The regulation of ICAM-1 at the protein level was confirmed in Northern blot analysis for detection of ICAM-1 message. In these experiments, HUVEC were cultured for 3 days with bFGF and treated for the last 4 and 24 hours with PF4 (100 µg/ml). TNFα was added 2 hours before isolation of RNA. RNA from a subconfluent EC cultures (75 cm² Petri-dishes) incubated with bFGF for different time-points was isolated using an RNA-zol kit (Campro Scientific, Houston, Tex.). Total RNA (10 µg) for each sample was separated in a 0.8% formaldehyde-denaturing gel, transferred to nitrocellulose (Hybond N+, Amersham International, Amersham, UK) and hybridized to a ³²P-labelled 1.9 Kb c-DNA probe, containing the functional sequence of the human ICAM-1 gene (a gift from Dr. B. Seed). Membranes were washed at a high stringency in 0.2×SSC, 0.1% SDS at 50° C. for 1 hour. Filters were exposed to X-ray films (Kodak X-omat, Eastman Kodak Company, Rochester, N.Y.) using an intensifying screen at −80° C. for not less than 12 hr. Autoradiograms were subjected to scanning using a laser densitometer (Model GS670, Bio-Rad, Hercules, Calif.) and data were analysed with the Molecular Analyst PC™ software. The intensity of the major ICAM-1 mRNA transcript was normalized with respect to actin mRNA expression used as a control.

Functional impact for the observed phenomena was provided by leukocyte/EC adhesion assays as described earlier (Griffioen et al. Cancer Res. 56:1111–1117, 1996). The bFGF mediated inhibition of leukocyte adhesion to cultured HUVEC was completely abolished in the presence of PF4 or related peptides. TNF mediated upregulation of adhesion to bFGF preincubated HUVEC in the presence of PF4 was similar to the adhesion to TNF treated control cells. PHA-activated peripheral blood T lymphocyte were adhered for 1 hour at 37° C. to TNF-α (4 ng/ml), bFGF (10 ng/ml)+PF4 (100 µg/ml) treated, or control (HUVEC). Non-adhering cells were removed and adhered cells were enumerated by an inverted microscope. Values of one representative experiment out of three are expressed as numbers of adhered cells per high power field. Statistical significance is determined by the Student's t-test.

These results indicate that the inhibition of angiogenesis and endothelial cell proliferation, which has been demonstrated to prevent outgrowth of solid tumors and metastases, is able to overcome the down regulation of adhesion molecules and the anergy upon stimulation with inflammator cytokines. In experiments to document the effect of other inhibitors of angiogenesis the same results were found for thrombospondin-1 and IP-10. However, the metalloproteinase inhibitor BB-94 (batimastat) and thalidomide, which do not affect EC growth in vitro, did not affect ICAM-1 expression. We concluded that the ICAM-1 regulation coincides with the regulatory mechanisms involving EC growth. The present results indicate that adhesion molecules which are necessary for the formation of an efficient leukocyte infiltrate are not only under regulation of angiogenic factors but are induced under conditions of angiogenesis inhibition. Specific inhibition of EC growth in vivo and regulation of EAM is therefore a powerful tool in cancer therapy. Definition of synthetic non-endogenous active peptides (such as βpep type peptides, including βpep-14) will contribute to this approach.

TABLE 7

INHIBITION OF EC-PROLIFERATION (³H)-THYMIDINE INCORPORATION BY DIFERENT ANTIOGENESIS INHIBITORS

|  | no bFGF | 10 ng/ml bFGF |
|---|---|---|
| expt 1 | | |
| medium | 4044 ± 206 | 28815 ± 1007 |
| PF4 (1 µg/ml) | 4656 ± 456 | 28782 ± 815 |
| PF4 (10 µg/ml) | 4066 ± 351 | 23868 ± 402 |
| PF4 (100 µg/ml) | 1651 ± 172 | 4655 ± 421 |
| expt 2 | | |
| medium | 14296 ± 2490 | 29079 ± 2506 |
| βpep-14 (1 µg/ml) | 14184 ± 1775 | 28695 ± 1062 |
| βpep-14 (10 µg/ml) | 9886 ± 2114 | 29530 ± 1608 |
| βpep-14 (100 µg/ml) | 3774 ± 299 | 6585 ± 132 |
| βpep-16 (1 µg/ml) | 15039 ± 2020 | 35447 ± 2621 |
| βpep-16 (10 µg/ml) | 11881 ± 2545 | 33663 ± 2572 |
| βpep-16 (100 µg/ml) | 4929 ± 749 | 7852 ± 875 |
| expt 2 | | |
| medium | 6780 ± 713 | 52808 ± 4092 |
| PF4 (1 µg/ml) | 6171 ± 1227 | 43524 ± 5318 |
| PF4 (10 µg/ml) | 3547 ± 317 | 8337 ± 704 |
| PF4 (100 µg/ml) | 947 ± 170 | 1654 ± 375 |
| βpep-14 (1 µg/ml) | 7214 ± 1668 | 48443 ± 2700 |
| βpep-14 (10 µg/ml) | 6074 ± 899 | 52126 ± 1258 |
| βpep-14 (100 µg/ml) | 1062 ± 325 | 7663 ± 715 |
| βpep-16 (1 µg/ml) | 7450 ± 737 | 47727 ± 447 |
| βpep-16 (10 µg/ml) | 6148 ± 1370 | 44919 ± 2081 |
| βpep-16 (100 µg/ml) | 2669 ± 370 | 27071 ± 3277 |
| expt 3 | | |
| medium | ND | 3432 ± 232 |
| IP-10 (100 µg/ml) | ND | 725 ± 95 |
| expt 4 | | |
| medium | 18904 ± 1501 | 31954 ± 1220 |
| TSP-1 (10 µg/ml) | 8865 ± 639 | 22338 ± 860 |
| TSP-1 (25 µg/ml) | 5565 ± 349 | 10267 ± 797 |

Figure 7:
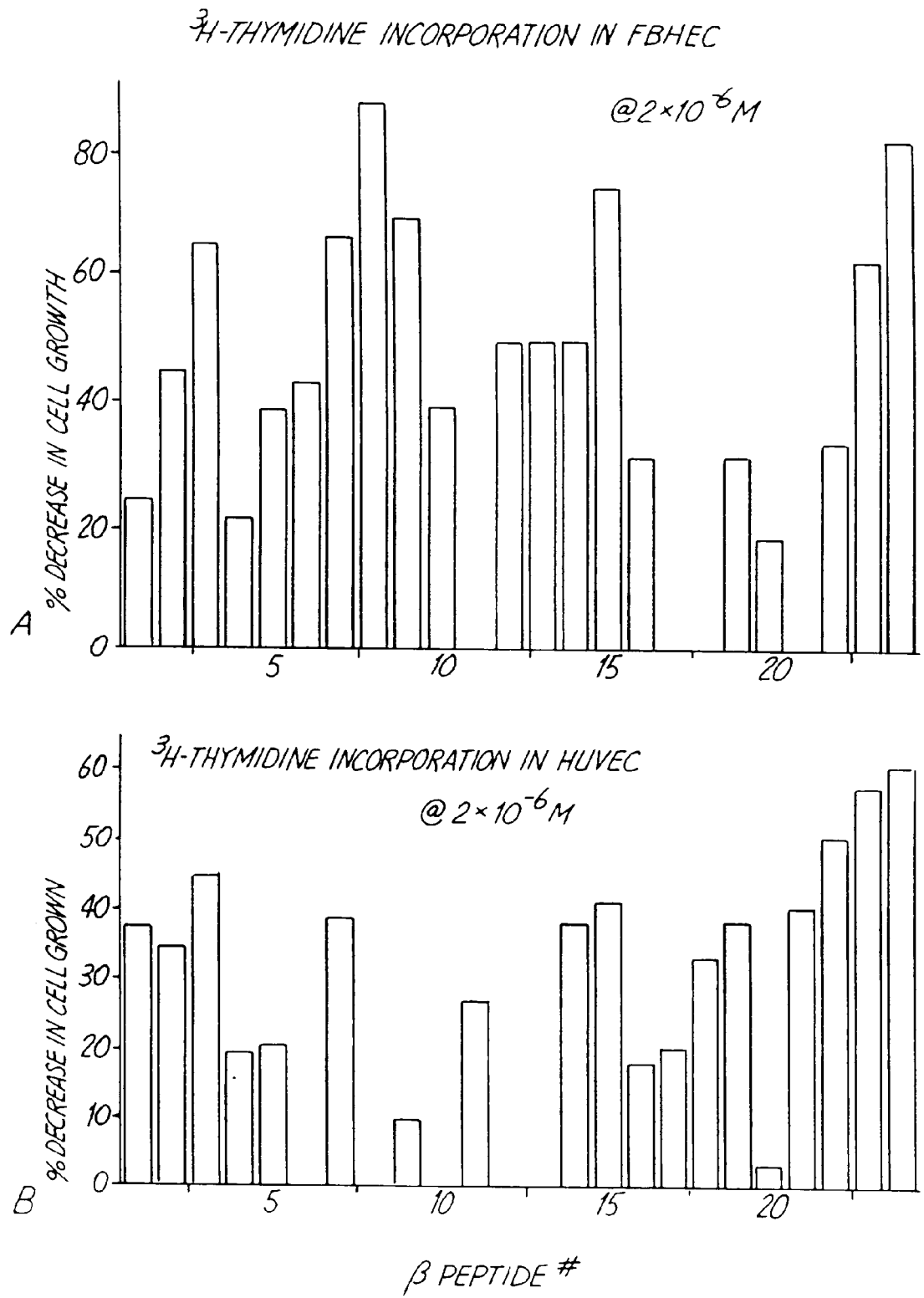
FIG. 7 provides $^3$H-Thymidine incorporation data for two different types of endothelial cells with peptide (βpep-1 through βpep-24) concentrations of $2 \times 10^{-6}$ M.
Figure 8:
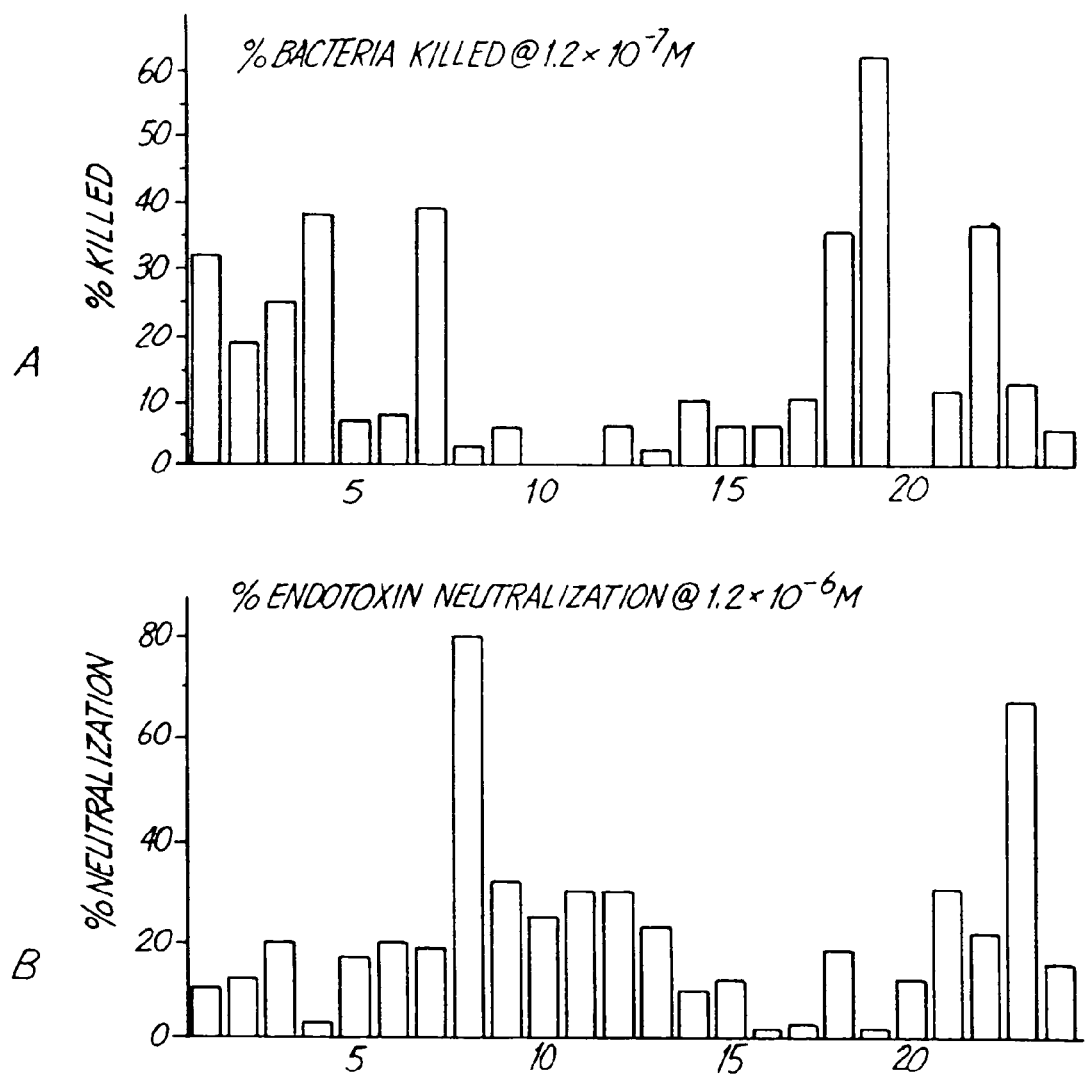
FIG. 8A illustrates the P. aeruginosa bactericidal activity of βpep-1 through βpep-24 at a peptide concentration of $1.2 \times 10^{-7}$ M
FIG. 8B illustrates the endotoxin neutralizing activity of βpep-1 through βpep-24 at a peptide concentration of $1.2 \times 10^{-6}$ M.

EC proliferation was measured using a ³[H]thymidine incorporation assay. EC were seeded in flatbottomed 96-well tissue culture plates (5000 cells/well) and grown for 3 days, in culture medium. In some cultures the proliferation of EC was enhanced by incubation with 10 ng/ml bFGF. During the list 6 hours of the assay, the culture was pulsed with 0.5 µCi [methyl-³H]thymidine/well. Results are expressed as the arithmetic mean counts per minute (cpm) of triplicate cultures.

βpeptides 1–24 were tested in an endothelial cell proliferation assay using $^3$H-thymidine incorporation. At least half of the peptides were somewhat active at 2.6 micromolar at decreasing endothelial cell growth. These results are provided in FIG. 7. βpep-23 and βpep-24 were about 30% effective at 0.26 micromolar.

The peptides were also able to regulate inter-cellular adhesion molecule (ICAM) expression. This receptor is downregulated in tumors and agents that are effective at upregulating ICAM are potentially useful therapeutic agents to control tumor growth. Those that were the most anti-angiogenic appeared to be least effective at ICAM regulation. That the βpeptides have the same or similar positive charge to mass ratios but do not share the same activities indicates that the peptides work specifically. For example, βpep-8 demonstrates little cell proliferation activity while βpep-24 was very good at controlling cell proliferation. Those skilled in the art will readily be able to use the assays provided here and the βpep sequences disclosed herein, along with methods for producing additional peptides according to this invention to identify peptides with ICAM upregulating activity and peptides with endothelial cell proliferation activity without undue experimentation.

All references cited herein are incorporated by reference, in their entirety, into this text. Although the invention has been described in the context of particular embodiments, it is intended that the scope of coverage of the patent be limited only by reference to the following claims.

What is claimed is:

1. A water soluble peptide comprising βpep-19 (SEQ ID NO:19).

2. The peptide of claim 1 further comprising a pharmaceutically acceptable carrier.

3. The peptide of claim 2 wherein said pharmaceutically acceptable carrier is selected from the group consisting of isotonic saline, dimethylsulfoxide, alcohol, phosphate buffered saline, and other balanced salt solutions.

4. The peptide of claim 1 conjugated to a protein carrier.

5. The peptide of claim 4 wherein said protein carrier is selected from the group consisting of keyhole limpet hemocyanin (KLH), bovine serum albumin (BSA), and ovalbumin.

6. A method for treating a bacteria infection comprising administering to a mammal an amount of a pharmaceutical composition effective to inhibit the bacterial infection, wherein the pharmaceutical composition comprises:
  (a) a peptide comprising βpep-19 (SEQ ID NO:19); and
  (b) a pharmaceutically acceptable carrier.

7. The method of claim 6 wherein the peptide is bactericidal.

8. A method for inhibiting TNF-α levels in a mammal comprising administering a therapeutically effective amount of a pharmaceutical composition comprising:
  (a) a peptide comprising βpep-19 (SEQ ID NO:19); and
  (b) a pharmaceutically acceptable carrier.

9. A method for inhibiting endothelial cell proliferation comprising administering to a mammal an effective amount of a composition comprising:
  a peptide comprising βpep-19 (SEQ ID NO:19).

10. A method for promoting inter-cellular adhesion molecule expression comprising administering to a mammal an effective amount of a composition comprising:
  a peptide comprising βpep-19 (SEQ ID NO:19).

11. A method for inhibiting angiogenesis in a cell culture, the method comprising contacting cells with an effective amount of a composition comprising a peptide comprising βpep-19 (SEQ ID NO:19).

12. A method for inhibiting angiogenesis in a mammal, the method comprising administering to the mammal an effective amount of a composition comprising a peptide comprising βpep-19 (SEQ ID NO:19); and a pharmaceutically acceptable carrier.

13. A method for inhibiting tumorigenesis in a mammal, the method comprising administering to the mammal an effective amount of a composition comprising a peptide comprising βpep-19 (SEQ ID NO:19) and a pharmaceutically acceptable carrier.

14. A method for inhibiting bacterial infection in a cell culture, the method comprising contacting cells with an effective amount of a composition comprising a peptide comprising βpep-19 (SEQ ID NO:19).

15. A method for inhibiting TNF-α levels in a cell culture, the method comprising contacting cells with an effective amount of a composition comprising a peptide comprising βpep-19 (SEQ ID NO:19).

16. A method for inhibiting endothelial cell proliferation in a cell culture, the method comprising contracting cells with an effective amount of a composition comprising:
  a peptide demonstrating endothelial cell proliferation inhibition comprising βpep-19 (SEQ ID NO:19).

17. A method for promoting inter-cellular adhesion molecule expression in a cell culture, the method comprising contacting cells with an effective amount of a composition comprising:
  a peptide comprising βpep-19 (SEQ ID NO:19).

18. A method for inhibiting inter-cellular adhesion molecule expression down regulation in a mammal, the method comprising administering to the mammal an effective amount of a composition comprising:
  a peptide comprising βpep-19 (SEQ ID NO:19).

19. A method for inhibiting inter-cellular adhesion molecule expression down regulation in a cell culture, the method comprising contacting cells with an effective amount of a composition comprising:
  a peptide comprising βpep-19 (SEQ ID NO:19).

20. A method for inhibiting leukocyte/endothelial cell adhesion in a cell culture, the method comprising contacting cells with an effective amount of a composition comprising βpep-19 (SEQ ID NO:19).

21. A method of increasing leukocyte cell infiltration in a mammal, the method comprising administering to the mammal an effective amount of a composition comprising βpep-19 (SEQ ID NO:19); and a pharmaceutically acceptable carrier.

* * * * *

UNITED STATES PATENT AND TRADEMARK OFFICE
CERTIFICATE OF CORRECTION

PATENT NO. : 7,030,087 B2  Page 1 of 1
APPLICATION NO. : 10/300083
DATED : April 18, 2006
INVENTOR(S) : Mayo et al.

It is certified that error appears in the above-identified patent and that said Letters Patent is hereby corrected as shown below:

Cover Page, (75) Inventors:
Delete "Beulah H. Gray, Ontario, OR (US); Judith R. Haseman, Eagan, MN (US):"

Signed and Sealed this

Eighteenth Day of July, 2006

JON W. DUDAS
*Director of the United States Patent and Trademark Office*

```
                        SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Lys Phe Ile Val Thr Leu Arg Val Ile Lys Ala Gly Pro His Ser Pro
1               5                   10                  15

Thr Ala Gln Ile Ile Val Glu Leu Lys Asn Gly Arg Lys Leu Ser Leu
                20                  25                  30

Asp (2) INFORMATION FOR SEQ ID NO: 2:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Ala Asn Ile Lys Leu Ser Val Glu Met Lys Leu Phe Lys Arg His Leu
1               5                   10                  15

Lys Trp Lys Ile Ile Val Lys Leu Asn Asp Gly Arg Glu Leu Ser Leu
                20                  25                  30

Asp (2) INFORMATION FOR SEQ ID NO: 3:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO: 3:

Ala Asn Ile Lys Leu Ser Val Glu Met Lys Leu Phe Cys Tyr Trp Lys
1               5                   10                  15

Val Cys Lys Ile Ile Val Lys Leu Asn Asp Gly Arg Glu Leu Ser Leu
            20                  25                  30

Asp (2) INFORMATION FOR SEQ ID NO: 4:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Ser Ile Gln Asp Leu Asn Val Ser Met Lys Leu Phe Arg Lys Gln Ala
1               5                   10                  15

Lys Trp Lys Ile Ile Val Lys Leu Asn Asp Gly Arg Glu Leu Ser Leu
            20                  25                  30

Asp (2) INFORMATION FOR SEQ ID NO: 5:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Ala Asn Ile Lys Leu Ser Val Lys Trp Lys Ala Gln Lys Arg Phe Leu
1               5                   10                  15

Lys Met Ser Ile Asn Val Asp Leu Ser Asp Gly Arg Glu Leu Ser Leu
            20                  25                  30

Asp (2) INFORMATION FOR SEQ ID NO: 6:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

His Ile Lys Glu Leu Gln Val Lys Trp Lys Ala Gln Lys Arg Phe Leu
1               5                   10                  15

Lys Met Ser Ile Ile Val Lys Leu Asn Asp Gly Arg Glu Leu Ser Leu
            20                  25                  30

Asp (2) INFORMATION FOR SEQ ID NO: 7:

(i) SEQUENCE CHARACTERISTICS:
        (A) LENGTH: 33 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO: 7:

Ser Ile Gln Asp Leu Asn Val Ser Met Lys Leu Phe Arg Lys Gln Ala
1               5                   10                  15
Lys Trp Lys Ile Asn Val Lys Leu Asn Asp Gly Arg Glu Leu Ser Leu
            20                  25                  30
Asp (2) INFORMATION FOR SEQ ID NO: 8:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

His Ile Lys Glu Leu Gln Val Arg Trp Arg Ala Gln Lys Arg Phe Leu
1               5                   10                  15
Arg Met Ser Ile Ile Val Lys Leu Asn Asp Gly Arg Glu Leu Ser Leu
            20                  25                  30
Asp (2) INFORMATION FOR SEQ ID NO: 9:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

His Ile Lys Glu Leu Gln Val Lys Met Lys Ala Gln Lys Arg Phe Leu
1               5                   10                  15
Lys Trp Ser Ile Ile Val Lys Leu Asn Asp Gly Arg Glu Leu Ser Leu
            20                  25                  30
Asp (2) INFORMATION FOR SEQ ID NO: 10:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Ala Asn Ile Lys Leu Ser Val Lys Trp Lys Ala Gln Lys Arg Phe Leu
1               5                   10                  15
Lys Met Ser Ile Ile Val Lys Leu Asn Asp Gly Arg Glu Leu Ser Leu
            20                  25                  30
Asp
```

(2) INFORMATION FOR SEQ ID NO: 11:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Ala Asn Ile Lys Leu Ser Val Glu Met Lys Leu Phe Cys Arg His Leu
1               5                   10                  15

Lys Cys Lys Ile Ile Val Lys Leu Asn Asp Gly Arg Glu Leu Ser Leu
            20                  25                  30

Asp (2) INFORMATION FOR SEQ ID NO: 12:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Ala Asn Ile Lys Leu Ser Val Glu Met Lys Phe Phe Lys Arg His Leu
1               5                   10                  15

Lys Trp Lys Ile Ile Val Lys Leu Asn Asp Gly Arg Glu Leu Ser Leu
            20                  25                  30

Asp (2) INFORMATION FOR SEQ ID NO: 13:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Ala Asn Ile Lys Leu Ser Val Glu Phe Lys Leu Phe Lys Arg His Leu
1               5                   10                  15

Lys Trp Lys Ile Ile Phe Lys Leu Asn Asp Gly Arg Glu Phe Ser Leu
            20                  25                  30

Asp (2) INFORMATION FOR SEQ ID NO: 14:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Ser Ile Gln Asp Leu Asn Val Ser Met Lys Leu Phe Arg Lys Gln Ala
1               5                   10                  15

Lys Trp Lys Leu Ile Val Lys Leu Asn Asp Gly Arg Glu Leu Ser Leu

```
            20                  25                  30
Asp (2) INFORMATION FOR SEQ ID NO: 15:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Ser Ile Gln Asp Leu Asn Val Ser Met Lys Leu Phe Arg Lys Gln Ala
1               5                  10                  15

Lys Trp Lys Ile Ile Leu Lys Leu Asn Asp Gly Arg Glu Leu Ser Leu
            20                  25                  30

Asp (2) INFORMATION FOR SEQ ID NO: 16:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Ser Ile Gln Asp Leu Asn Val Ser Met Lys Leu Phe Arg Lys Gln Ala
1               5                  10                  15

Lys Trp Lys Ile Ile Ala Lys Leu Asn Asp Gly Arg Glu Leu Ser Leu
            20                  25                  30

Asp (2) INFORMATION FOR SEQ ID NO: 17:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Ser Ile Gln Asp Leu Asn Val Ser Met Lys Leu Phe Arg Lys Gln Ala
1               5                  10                  15

Lys Trp Lys Ile Leu Val Lys Leu Asn Asp Gly Arg Glu Leu Ser Leu
            20                  25                  30

Asp (2) INFORMATION FOR SEQ ID NO: 18:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:
```

```
Ser Ile Gln Asp Leu Lys Val Ser Met Lys Leu Phe Arg Lys Gln Ala
1               5                  10                 15

Lys Trp Lys Ile Ile Val Lys Leu Asn Asp Gly Arg Glu Leu Ser Leu
            20                  25                 30

Asp (2) INFORMATION FOR SEQ ID NO: 19:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Ser Ile Gln Lys Leu Asn Val Ser Met Lys Leu Phe Arg Lys Gln Ala
1               5                  10                 15

Lys Trp Lys Ile Ile Val Lys Leu Asn Asp Gly Arg Glu Leu Ser Leu
            20                  25                 30

Asp (2) INFORMATION FOR SEQ ID NO: 20:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Ser Ile Gln Asp Leu Asn Val Ser Met Xaa Leu Phe Arg Lys Gln Ala
1               5                  10                 15

Lys Trp Lys Ile Ile Val Lys Leu Asn Asp Gly Arg Glu Leu Ser Leu
            20                  25                 30

Asp (2) INFORMATION FOR SEQ ID NO: 21:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Ser Ile Gln Asp Leu Asn Val Ser Leu Lys Leu Phe Arg Lys Gln Ala
1               5                  10                 15

Lys Trp Lys Ile Ile Val Lys Leu Asn Asp Gly Arg Glu Leu Ser Leu
            20                  25                 30

Asp (2) INFORMATION FOR SEQ ID NO: 22:

(i) SEQUENCE CHARACTERISTICS:
        (A) LENGTH: 33 amino acids
        (B) TYPE: amino acid
        (C) STRANDEDNESS: single
```

-continued (D) TOPOLOGY: linear (ii) MOLECULE TYPE: peptide (xi) SEQUENCE DESCRIPTION: SEQ ID NO: 22:

Ser Ile Gln Asp Leu Asn Leu Ser Met Lys Leu Phe Arg Lys Gln Ala
1               5                   10                  15

Lys Trp Lys Ile Ile Val Lys Leu Asn Asp Gly Arg Glu Leu Ser Leu
            20                  25                  30

Asp (2) INFORMATION FOR SEQ ID NO: 23:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Ser Ile Gln Asp Leu Lys Val Ser Leu Asn Leu Phe Arg Lys Gln Ala
1               5                   10                  15

Lys Trp Lys Ile Ile Val Lys Leu Asn Asp Gly Arg Glu Leu Ser Leu
            20                  25                  30

Asp (2) INFORMATION FOR SEQ ID NO: 24:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Ser Ile Gln Phe Leu Lys Val Ser Leu Asn Leu Asp Arg Lys Gln Ala
1               5                   10                  15

Lys Trp Lys Ile Ile Val Lys Leu Asn Asp Gly Arg Glu Leu Ser Leu
            20                  25                  30

Asp (2) INFORMATION FOR SEQ ID NO: 25:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Ala Asn Ile Lys Leu Ser Val Gln Met Lys Leu Phe Lys Arg His Leu
1               5                   10                  15

Lys Trp Lys Ile Ile Val Lys Leu Asn Asp Gly Arg Glu Leu Ser Leu
            20                  25                  30

Asp (2) INFORMATION FOR SEQ ID NO: 26:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 26:

Ser Ile Gln Asp Leu Asn Val Ser Met Lys Leu Phe Arg Lys Gln Ala
1               5                   10                  15

Lys Trp Lys Ile Ile Ile Lys Leu Asn Asp Gly Arg Glu Leu Ser Leu
            20                  25                  30

Asp (2) INFORMATION FOR SEQ ID NO: 27:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 27:

Ser Ile Gln Asp Leu Asn Val Ser Met Lys Leu Phe Arg Lys Gln Ala
1               5                   10                  15

Lys Trp Lys Ala Ile Val Lys Leu Asn Asp Gly Arg Glu Leu Ser Leu
            20                  25                  30

Asp (2) INFORMATION FOR SEQ ID NO: 28:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 28:

Ser Ile Gln Asp Leu Asn Val Ser Met Lys Leu Phe Arg Lys Gln Ala
1               5                   10                  15

Lys Trp Lys Val Ile Val Lys Leu Asn Asp Gly Arg Glu Leu Ser Leu
            20                  25                  30

Asp (2) INFORMATION FOR SEQ ID NO: 29:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 29:

Ser Ile Gln Asp Leu Asn Val Ser Met Lys Leu Phe Arg Lys Gln Ala
1               5                   10                  15

Lys Trp Lys Leu Ile Leu Lys Leu Asn Asp Gly Arg Glu Leu Ser Leu
            20                  25                  30

Asp (2) INFORMATION FOR SEQ ID NO: 30:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

```
Ser Ile Gln Asp Leu Asn Val Ser Met Lys Leu Phe Arg Lys Gln Ala
1               5                   10                  15
Lys Trp Lys Val Ile Ile Lys Leu Asn Asp Gly Arg Glu Leu Ser Leu
            20                  25                  30
Asp
```

(2) INFORMATION FOR SEQ ID NO: 31:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

```
Asn Ala Asn Ile Lys Ile Ser Gly Lys Trp Lys Ala Gln Lys Arg Phe
1               5                   10                  15
Leu Lys Met Ser Gly Asn Phe Asp Leu Ser Ile
            20                  25
```

(2) INFORMATION FOR SEQ ID NO: 32:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

```
Met Asn Ser Gln Val Cys Glu Lys Val Thr Asn Ser Val Ser Ser Lys
1               5                   10                  15
Leu Gln Pro Tyr Phe Gln Thr Leu Pro Val Met Thr Lys Ile
            20                  25                  30
```

(2) INFORMATION FOR SEQ ID NO: 33:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

```
Leu Xaa Xaa Gly Arg
1               5
```

(2) INFORMATION FOR SEQ ID NO: 34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

```
Lys Xaa Xaa Gly Arg
1               5
```

(2) INFORMATION FOR SEQ ID NO: 35:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Ile Ile Val Lys Leu Ser Asp Gly Arg Glu Leu Ser Leu Asp
1               5                   10
```

(2) INFORMATION FOR SEQ ID NO: 36:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
Arg His Ile Thr Ser Leu Glu Val Ile Lys Ala Gly Pro His Ser Pro
1               5                   10                  15
Thr Ala Gln Leu Ile Ala Thr Leu Lys Asn Gly Arg Lys Ile Ser Leu
            20                  25                  30
Asp
```

(2) INFORMATION FOR SEQ ID NO: 37:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Lys Phe Ile Lys Glu Leu Arg Val Ile Glu Ser Gly Pro His Ser Ala
1               5                   10                  15
Asn Thr Glu Ile Ile Val Lys Leu Ser Asp Gly Arg Glu Leu Ser Leu
            20                  25                  30
Asp
```

(2) INFORMATION FOR SEQ ID NO: 38:

(i) SEQUENCE CHARACTERISTICS:
        (A) LENGTH: 33 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO: 38:

Lys Asn Ile Gln Ser Val Asn Val Lys Ser Pro Gly Pro His Ser Ala
1               5                   10                  15

Gln Thr Glu Val Ile Ala Thr Leu Lys Asn Gly Arg Lys Ala Ser Leu
            20                  25                  30

Asn
```